(12) United States Patent
Fuchiwaki

(10) Patent No.: US 12,326,445 B2
(45) Date of Patent: Jun. 10, 2025

(54) ASSAY DEVICE

(71) Applicant: NATIONAL INSTITUTE OF ADVANCED INDUSTRIAL SCIENCE AND TECHNOLOGY, Tokyo (JP)

(72) Inventor: Yusuke Fuchiwaki, Takamatsu (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 1149 days.

(21) Appl. No.: 17/269,876

(22) PCT Filed: Aug. 29, 2019

(86) PCT No.: PCT/JP2019/033846
§ 371 (c)(1),
(2) Date: Feb. 19, 2021

(87) PCT Pub. No.: WO2020/045551
PCT Pub. Date: Mar. 5, 2020

(65) Prior Publication Data
US 2021/0170398 A1    Jun. 10, 2021

(30) Foreign Application Priority Data

Aug. 31, 2018  (JP) .................................. 2018-163492

(51) Int. Cl.
*G01N 33/543* (2006.01)
*B01L 3/00* (2006.01)
*G01N 33/53* (2006.01)

(52) U.S. Cl.
CPC .... *G01N 33/54388* (2021.08); *B01L 3/50273* (2013.01); *G01N 33/5304* (2013.01);
(Continued)

(58) Field of Classification Search
CPC ......... G01N 33/54388; G01N 33/5304; G01N 35/08; G01N 37/00; B01L 3/50273;
(Continued)

(56) References Cited

U.S. PATENT DOCUMENTS 5,104,813 A * 4/1992 Besemer .................. G01N 1/38
422/106
5,230,866 A * 7/1993 Shartle .............. B01L 3/502723
422/68.1
(Continued)

FOREIGN PATENT DOCUMENTS

EP        2902784 A1   8/2015
JP     2010515877 A    5/2010
(Continued)

OTHER PUBLICATIONS

"Communication with Supplementary European Search Report", EP Application No. 19853568.4, Apr. 21, 2022, 8 pp.
(Continued)

*Primary Examiner* — William H. Beisner
*Assistant Examiner* — Danielle B Henkel
(74) *Attorney, Agent, or Firm* — Myers Bigel, P.A.

(57) ABSTRACT

An assay device allows enhancement of the liquid control performance. The assay device of the present invention includes a microflow passage 1, 31, 41 which allows flow of the liquid, an absorbing porous medium 2, 42 disposed at a distance from one end of the microflow passage, and a separating space 3, 43 disposed between the one end of the microflow passage and the absorbing porous medium. The assay device further includes two sideways ventilation passages 6, 46 which are adjacent to both sides of the microflow passage, respectively in the width direction orthogonal to the
(Continued)

flow direction, the two sideways ventilation passages 6, 46 being communicated with the microflow passage to allow air circulation.

9 Claims, 11 Drawing Sheets

(52) U.S. Cl.
CPC ............... *B01L 2300/0681* (2013.01); *B01L 2300/0816* (2013.01); *B01L 2300/0825* (2013.01); *B01L 2300/0896* (2013.01); *B01L 2400/0406* (2013.01); *B01L 2400/086* (2013.01); *B01L 2400/088* (2013.01)

(58) Field of Classification Search
CPC ..... B01L 2300/0681; B01L 2300/0816; B01L 2300/0825; B01L 2300/0896; B01L 2400/0406; B01L 2400/086; B01L 2400/088; B01L 2200/0684; B01L 2300/0874; B01L 2300/089; B01L 2300/161; B01L 2400/0457; B01L 3/5023; B01L 3/502723; B01L 2300/0887
See application file for complete search history.

(56) References Cited

U.S. PATENT DOCUMENTS

| | | | |
|---|---|---|---|
| 6,046,057 | A | 4/2000 | Nazareth et al. |
| 6,277,650 | B1 | 8/2001 | Nazareth et al. |
| 8,323,587 | B2 | 12/2012 | Suzuki et al. |
| 8,821,812 | B2* | 9/2014 | Ohman ................. B01L 3/5023 422/503 |
| 9,606,112 | B2* | 3/2017 | Ohman ............. B01L 3/502746 |
| 9,623,407 | B2* | 4/2017 | Delamarche ........ B01F 33/3017 |
| 9,744,534 | B2 | 8/2017 | Fuchiwaki et al. |
| 11,396,013 | B2* | 7/2022 | Wang ................. B01L 3/502707 |
| 2002/0019062 | A1* | 2/2002 | Lea ................... B01L 3/502753 435/287.2 |
| 2009/0263288 | A1 | 10/2009 | Suzuki et al. |
| 2011/0011781 | A1 | 1/2011 | Blankenstein et al. |
| 2011/0036152 | A1 | 2/2011 | Park et al. |
| 2015/0219623 | A1 | 8/2015 | Doria et al. |
| 2015/0266023 | A1 | 9/2015 | Fuchiwaki et al. |
| 2017/0328896 | A1 | 11/2017 | Luloh et al. |
| 2018/0207564 | A1 | 7/2018 | Hennessey |

FOREIGN PATENT DOCUMENTS

| | | |
|---|---|---|
| JP | 2015172492 A | 10/2015 |
| JP | 6037184 B2 | 11/2016 |
| JP | 5291343 B2 | 9/2018 |
| WO | 9922238 A1 | 5/1999 |
| WO | 2008049083 A2 | 4/2008 |
| WO | 2017143323 A1 | 8/2017 |

OTHER PUBLICATIONS

"International Search Report and English language translation", International Application No. PCT/JP2019/033846, Nov. 19, 2019, 2 pp.

"Notice of Reasons for Rejection and English language translation", JP Application No. 2020-539576, Sep. 28, 2021, 8 pp.

* cited by examiner

ASSAY DEVICE

RELATED APPLICATIONS

This application is a 35 U.S.C. § 371 national stage application of PCT Application No. PCT/JP2019/033846, filed on Aug. 29, 2019, which claims priority from Japanese Patent Application No. 2018-163492, filed on Aug. 31, 2018, the contents of which are incorporated herein by reference in their entireties. The above-referenced PCT International Application was published in the Japanese language as International Publication No. WO 2020/045551 A1 on Mar. 5, 2020.

TECHNICAL FIELD

The present invention relates to an assay device configured to perform an assay using a liquid.

BACKGROUND ART

Primarily in the fields of biology, chemistry, and the like, assay devices including microflow passages have been employed for performing, for example, inspections, experiments, and assays using very small quantities of liquids such as reagents, processing agents, and the like on the order of a µl (1 microliter), that is to say, in the range from approximately 1 µl or more to less than approximately 1 ml. As such assay devices, an assay device of the lateral flow type, an assay device of the flow through type, and the like have recently been used for the purpose of reducing costs, improving operability, durability and liquid control performance, and the like.

In particular, the assay device of the lateral flow type is simply configured to move and operate the liquid using capillary phenomena of hydrophilic porous media, such as paper, cellulose membranes, and the like. The assay device of the lateral flow type may be produced at low cost, requiring no external mechanisms, such as pumps and the like, and no complicated operations, allowing improvement in durability. The assay device of the lateral flow type is employed for detecting or quantifying the concentration of antibodies or antigens contained in a sample through the ELISA (Enzyme-Linked Immuno Sorbent Assay) process, immunochromatography, and the like, in particular.

In an exemplary case of the assay device, the channel and the assay region connected to the channel, are provided in a plurality of layered porous media. The channel and the assay region are defined by the barrier constituted by the photoresist polymer that has been absorbed over the entire region of the layered porous media in the thickness direction (for example, see Patent Document 1).

The inventor of the present invention has invented the assay device as another exemplary case. The assay device includes the microflow passage, the porous medium disposed at a distance from one end of the microflow passage, and the space between the one end of the microflow passage and the porous medium. In the assay device, the liquid flowing in the microflow passage, passes over the space to come in contact with the porous medium while being absorbed thereby, and the fluid is then separated by the space so as to be held in the microflow passage (for example, see Patent Document 2).

CITATION LIST

Patent Document

Patent Document 1: JP 2010-515877 A
Patent Document 2: JP 6037184 B

SUMMARY OF INVENTION

Technical Problem

In an exemplary case of the assay device, since the channel and the assay region are constituted by the porous medium, a large quantity of liquid, for example, a reagent must be continuously fed from the channel to the assay region so as to ensure fluidity. Since the flow rate of the reagent passing through the porous medium, is reduced, the time taken for determining the effect may be prolonged. As a result, flowability of the liquid may be deteriorated, and risk of non-specific adsorption in the channel or the assay region, may be increased.

In another exemplary case of the assay device, there may be a risk of non-specific adsorption of the specimen, reagent, impurities, or the like on the wall that defines the microflow passage. Viscosity, friction, and the like generated between the liquid flowing in the microflow passage, and the wall that defines the microflow passage, may cause a risk of deteriorating the liquid flow performance. In a case of using the pressure-sensitive adhesive, the adhesive, or the like for the wall that defines the microflow passage, a case of using the assay device provided with the layered structure including a plurality of layers for forming the microflow passage between those layers, or the like, viscosity of the pressure-sensitive adhesive, the adhesive, or the like, and variation in the interlayer distance for forming the microflow passage, may increase the risk of generating the non-specific adsorption, and may deteriorate liquid flow performance.

In exemplary cases of the assay device, the non-specific adsorption may cause the risk of reducing yields of assay, destabilizing background, and generating noise. In the foregoing circumstances, the detector configured to detect assay reactions by obtaining signals derived from the assay reactions, may fail to detect such signals accurately. Furthermore, an air gap may be generated in the liquid, and the air gap may reduce liquid flowability.

In another exemplary case of the assay device, the liquid in the porous medium is likely to evaporate earlier than the liquid in the microflow passage. The evaporation of the liquid in the porous medium may accelerate evaporation of the liquid in the microflow passage. Variation in the ventilation performance owing to individual differences in the porous medium and moisture level of the porous medium may cause unevenness in the air flow rate in the space. The reduced air flow rate owing to the unevenness may deteriorate the liquid exchange performance in the space, and therefore, meniscus tortuosity in one end of the microflow passage may be increased. As a result, residual liquid in the space may be generated. The residual liquid in the space is particularly undesirable in view of preventing contamination.

The liquid control performance may be deteriorated by the prolonged time taken for determining the effect as mentioned above, generation of the non-specific adsorption, deterioration in the liquid flow performance, deterioration in the liquid exchange performance, the residual liquid, or the like. In other words, the assay device is required to improve the liquid control performance.

Solution to Problem

To solve the problem, the assay device according to an aspect includes a microflow passage configured to allow liquid to flow, an absorbing porous medium disposed at a distance from one end of the microflow passage, the one end being positioned on one side in a flow direction of the liquid, and a separating space disposed between the one end of the microflow passage and the absorbing porous medium. The assay device further includes two sideways ventilation passages being adjacent to both sides of the microflow passage, respectively in a width direction orthogonal to the flow direction, the two sideways ventilation passages being communicated with the microflow passage to allow air circulation.

The assay device according to another aspect includes a microflow passage configured to allow liquid to flow, a porous medium disposed at a distance from one end of the microflow passage, the one end being positioned on one side in a flow direction of the liquid, and a separating space disposed between the one end of the microflow passage and the porous medium. The assay device further includes a housing space housing the absorbing porous medium, a separating space wall defining the separating space in cooperation with the absorbing porous medium, the separating space wall including a top portion and a bottom portion defining the separating space on both sides in a height direction orthogonal to the flow direction and the width direction, and a guide wall protruding to the one side in the flow direction from the top portion or the bottom portion of the separating space wall in the housing space, the guide wall abuts the absorbing porous medium in the height direction, and the top portion or the bottom portion of the separating space wall, and the guide wall are formed to separate from the microflow passage in the height direction toward the one side from the other side in the flow direction.

Advantageous Effects of Invention

In the assay device according to this aspect, the liquid control performance can be enhanced.

DESCRIPTION OF EMBODIMENTS

Figure 2:
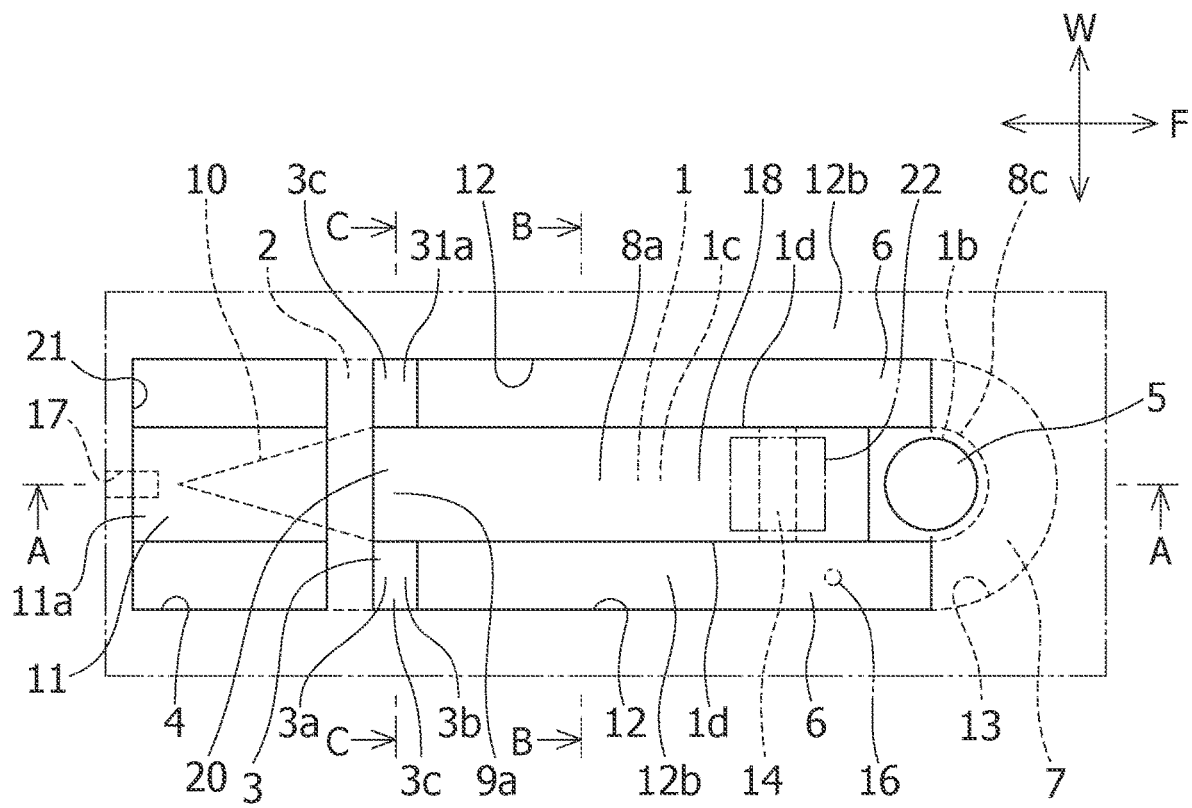
FIG. 2 is a schematic plan view showing the assay device according to the First Embodiment.
Figure 3:
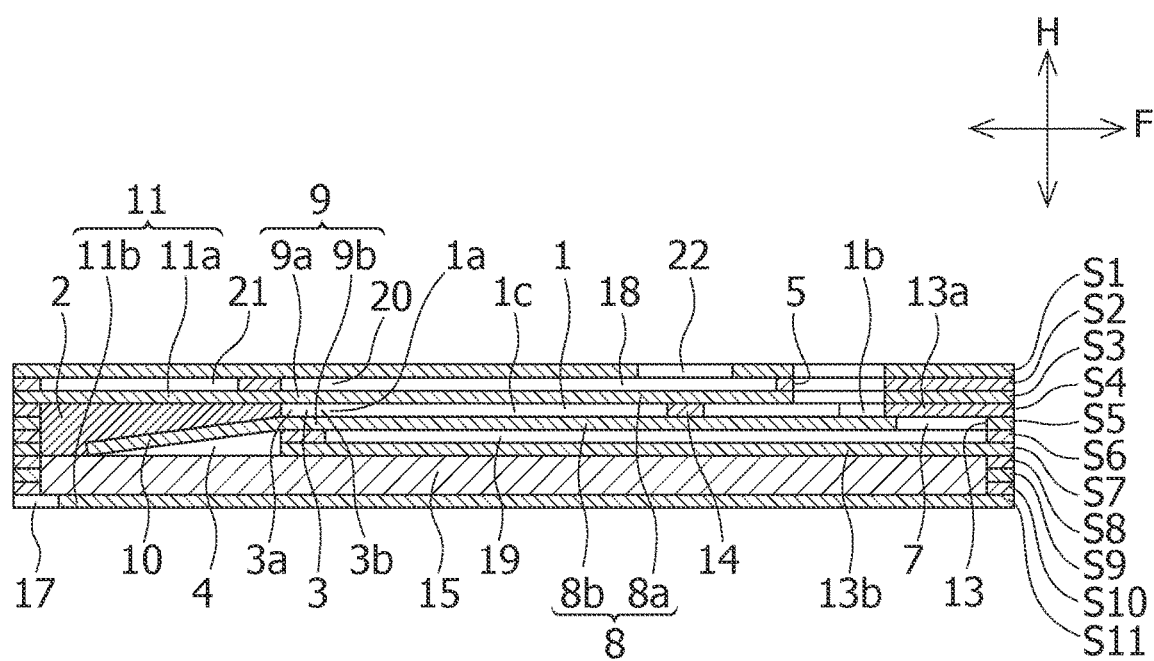
FIG. 3 is a sectional view taken along line A-A of FIG. 2.
Figure 4:
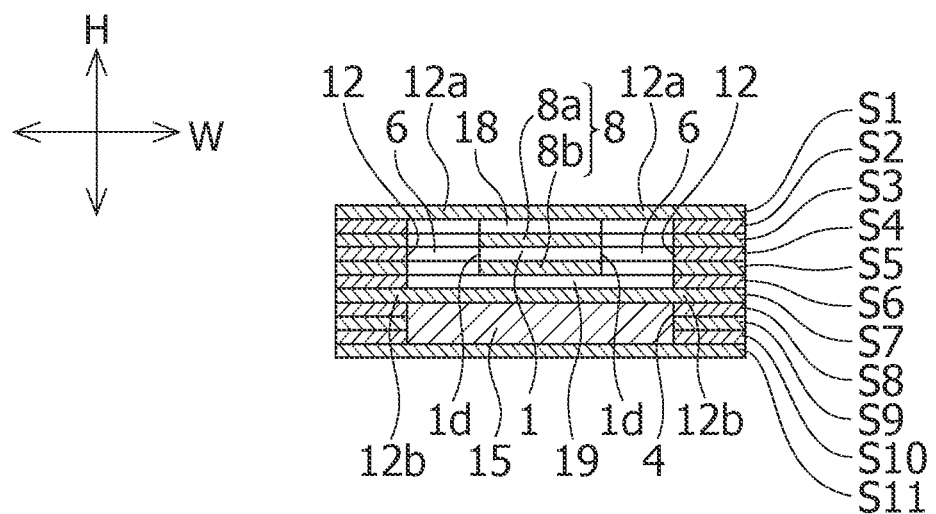
FIG. 4 is a sectional view taken along line B-B of FIG. 2.
Figure 5:
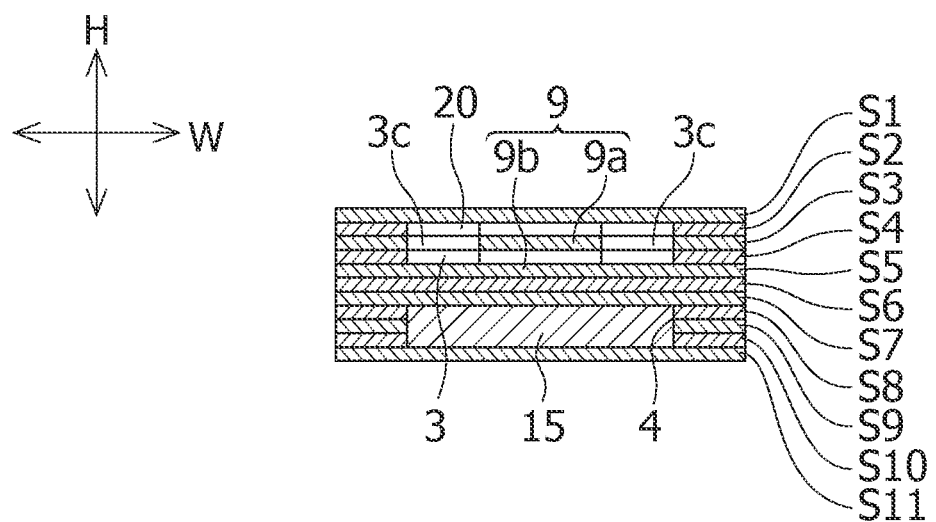
FIG. 5 is a sectional view taken along line C-C of FIG. 2.
Figure 6A:
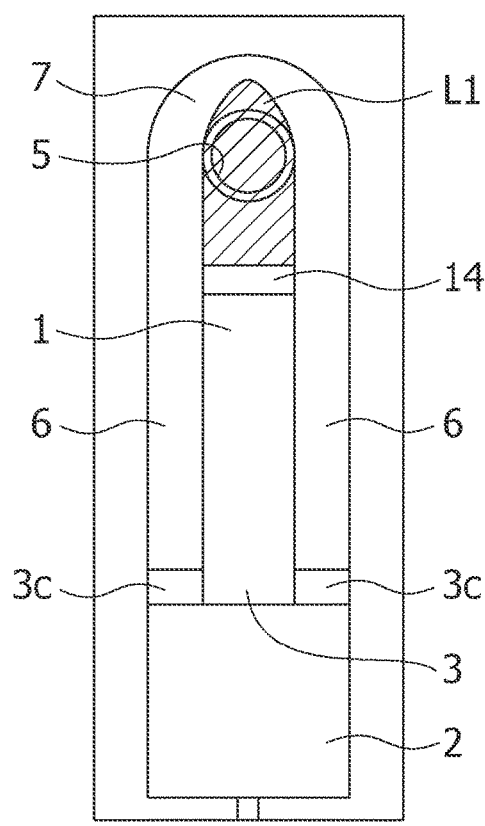
FIGS. 6(a) to 6(d) are plan views showing states in which sequential flows of the first liquid is supplied to the assay device according to the First Embodiment.
Figure 6B:
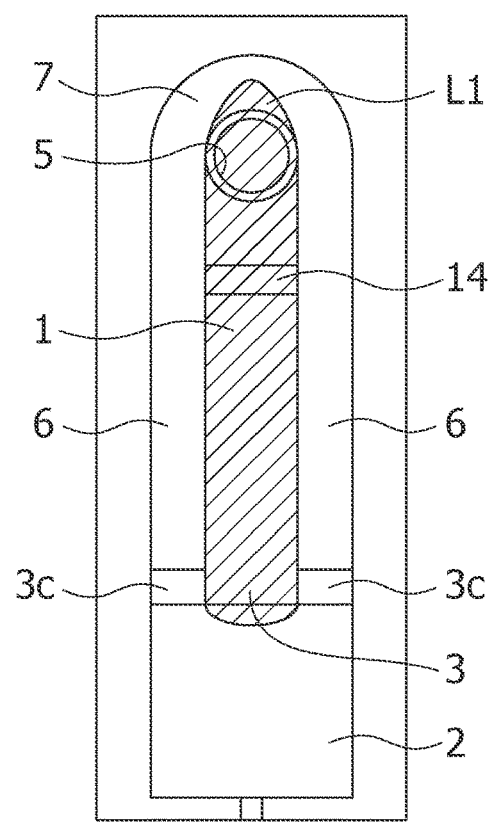
Figure 6C:
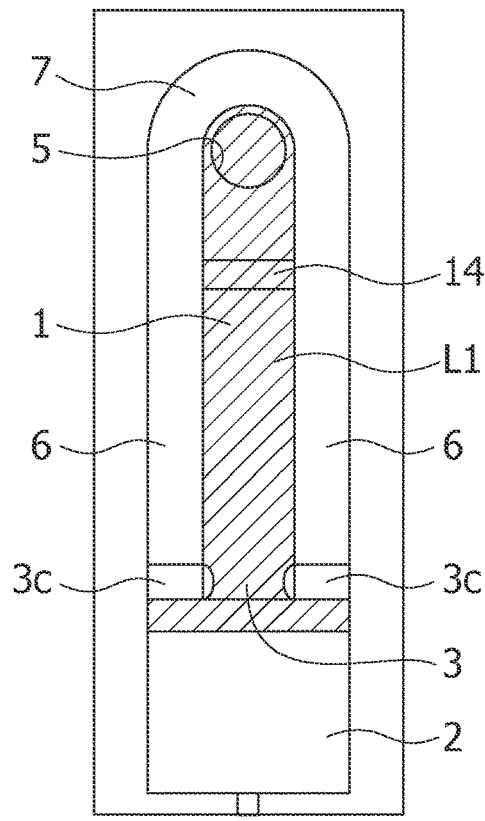
Figure 6D:
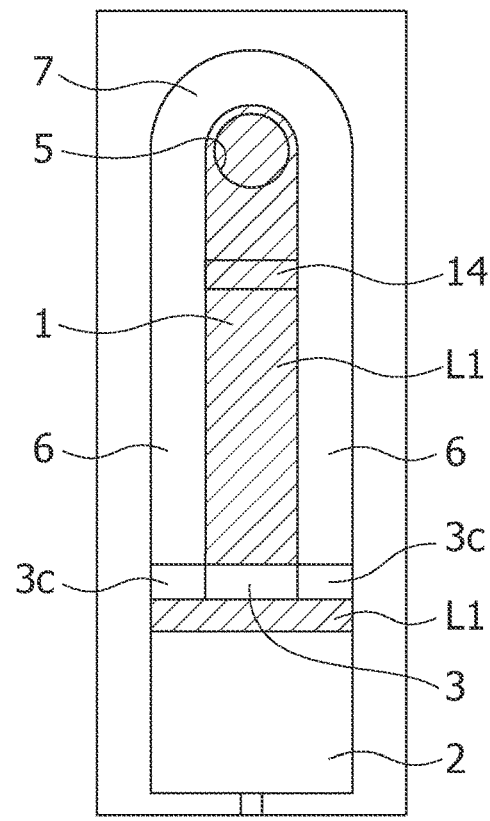
Figure 7A:
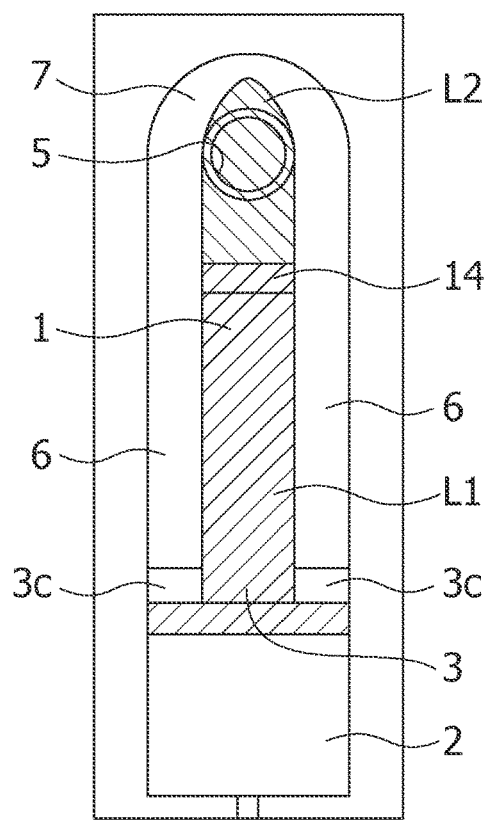
FIGS. 7(a) to 7(d) are plan views showing states in which sequential flows of the second liquid is supplied to the assay device according to the First Embodiment subsequent to supply of the first liquid.
Figure 7B:
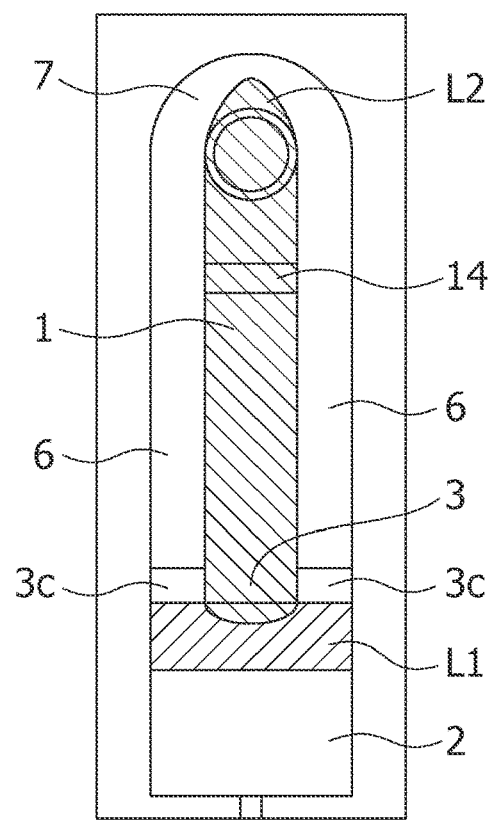
Figure 7C:
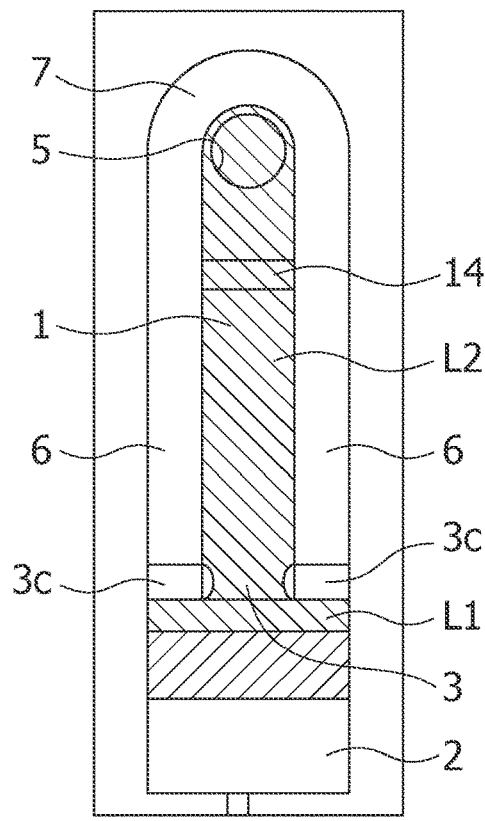
Figure 7D:
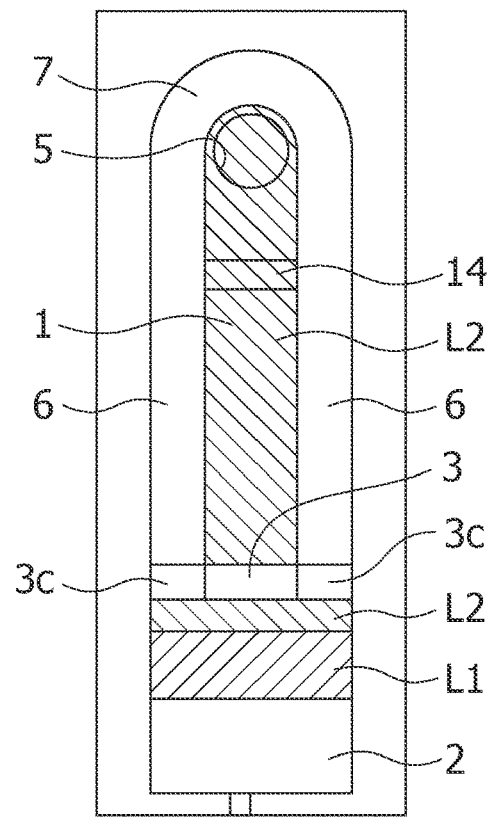

Assay devices according to the First and the Second Embodiments will be described. Referring to FIGS. 2, 8, 13 and 15, an outer shape of the assay device is expressed by a virtual line (that is, two-dot chain line), and components inside the assay device are expressed by solid lines and phantom lines (that is, broken lines). Although not specifically shown, each direction to which the assay device is oriented as shown in FIGS. 6(a) to 6(d), and FIGS. 7(a) to 7(d), is the same as the direction to which the assay device is oriented as shown in FIG. 2.

The liquid applicable to the assay device according to the Embodiment, is not restricted specifically so long as it is allowed to flow in the assay device. The liquid may typically contain water as a solvent, that is, it may be an aqueous solution. The liquid applicable to the assay device, may not only be produced as chemically pure liquid but also produced by dissolving, dispersing, or suspending gas, another liquid, or solid in the liquid.

The liquid may be hydrophilic. Liquid samples derived from an organism, may be used as the hydrophilic liquid, for example, whole blood, serum, blood plasma, urine, diluted solution of feces, saliva, cerebrospinal fluid, and/or the like of humans or animals. The use of these samples allows the assay device to effectively diagnostically measure a specimen in the liquid sample for the purpose of testing for pregnancy, urine, feces, adult diseases, allergies, infectious diseases, drugs, cancer, and/or the like. Suspension of food, drinking water, river water, soil-derived suspended solid, and/or the like may be used as the hydrophilic liquid. The use of such liquid allows the assay device to measure pathogens contained in food and drinking water, or contaminants in the river water and the soil.

In the specification, the "lateral flow" denotes the flow of liquid moved by gravitational sedimentation as the drive force. The movement of liquid based on the lateral flow denotes the liquid movement dominantly (prevailingly) caused by the liquid drive force generated by gravitational sedimentation. The movement of the liquid based on capillary force (capillary phenomenon), denotes the liquid movement predominantly (prevailingly) caused by interfacial tension. The liquid movement based on lateral flow, differs from the liquid movement based on capillary force.

In the specification, the "specimen" denotes the chemical compound or composition to be detected or measured using the liquid. For example, the "specimen" may be saccharides (for example, glucose), proteins or peptides (for example, serum proteins, hormones, enzymes, immunoregulatory factors, lymphokines, monokines, cytokines, glycoproteins, vaccine antigens, antibodies, growth factors, or multiplication factors), fats, amino acids, nucleic acids, steroids, vitamins, pathogens or antigens thereto, natural substances or synthetic chemicals, contaminants, medicines for therapeutic purpose or illegal drugs, metabolites of these substances, or those containing antibodies.

In the specification, the "microflow passage" denotes the flow passage configured to allow the liquid flow in the assay device in order to detect or measure the specimen using a very small quantity of liquid on the order of a μl (microliter), that is, ranging from approximately 1 μl or more to less than approximately 1 ml (milliliter), or in order to weigh a small quantity of liquid.

In the specification, the "film" denotes the membranous substance with thickness of approximately 200 μm (micrometer) or less, and the "sheet" denotes the membranous substance or tabular substance with thickness in excess of approximately 200 μm.

In the specification, the "plastic" denotes the polymerized or shaped material to be produced using polymerizable or polymer material as an essential component. The plastic includes polymer alloys formed by combining two or more kinds of polymers.

In the specification, the "porous medium" denotes a member having many micropores, which allows absorption and passage of the liquid therethrough, for example, paper, cellulose membranes, non-woven fabric, plastics, and/or the like. The "porous medium" may exhibit a hydrophilic property corresponding to the hydrophilic liquid, and exhibit a hydrophobic property corresponding to the hydrophobic liquid. The "porous medium" may exhibit the hydrophilic property, and may be formed as the paper. Furthermore, the "porous medium" may be formed as any one selected from the cellulose, cellulose nitrate, cellulose acetate, filter paper, tissue paper, toilet paper, paper towel, fabric, or a hydrophilic porous polymer through which water can pass.

First Embodiment

An assay device according to a First Embodiment will be described.
Outline of the Structure of Assay Device Referring to FIGS. 1 to 5, a schematic structure of the assay device according to this Embodiment will be described. The assay device includes a microflow passage 1 configured to allow liquid to flow. As described below, the direction along the liquid flow in the microflow passage 1 (as indicated by an arrow F), will be referred to as a "flow direction". In the Embodiment, the liquid flows toward one side of the microflow passage 1 from the other side. The one side in the flow direction will be defined as a downstream side, and the other side in the flow direction will be defined as an upstream side.

The assay device includes a first absorbing porous medium 2 disposed at a distance from one end 1a of the microflow passage 1, which is positioned at the one side (that is, downstream side) in the flow direction. The assay device includes a separating space 3 disposed between the one end 1a of the microflow passage 1 and the first absorbing porous medium 2. The separating space 3 is in the form of a cavity in the assay device. The first absorbing porous medium 2 is configured to ensure absorption of the liquid from the one end 1a of the microflow passage 1. The assay device includes a housing space 4 capable of housing the first absorbing porous medium 2. The housing space 4 is formed to continue to the separating space 3 in the flow direction.

The assay device includes an inlet 5 disposed in the other end 1b of the microflow passage 1, which is positioned at the other side (that is, upstream side) in the flow direction. The inlet 5 is configured to allow liquid to be supplied to the microflow passage 1. In the microflow passage 1, the liquid charged from the inlet 5, flows from the other end 1b to the one end 1a via an intermediate section 1c between the one end 1a and the other end 1b.

The assay device includes two adjacent sideways ventilation passages 6 at both sides of the microflow passage 1 in the width direction (indicated by an arrow W) substantially orthogonal to the flow direction. Each of the sideways ventilation passages 6 is configured to allow air circulation. The microflow passage 1 is communicated with the two sideways ventilation passages 6 in the width direction. The respective sideways ventilation passages 6 extend along the flow direction. In particular, the two sideways ventilation passages 6 may extend along both side edges 1d of the microflow passage 1 in the width direction.

The assay device further includes a connecting ventilation passage 7 which connects the two sideways ventilation passages 6 and extends around a circumference of the inlet 5. The connecting ventilation passage 7 is also configured to allow air circulation. The air circulation occurs in the two sideways ventilation passages 6 and the connecting ventilation passage 7, which are continuously connected to each other. Each of the other ends of the two sideways ventilation passages 6 at the other side in the flow direction, may be connected to the connecting ventilation passage 7. The assay device may be configured to include no connecting ventilation passage.

The assay device includes a microflow passage wall 8 that defines the microflow passage 1. The microflow passage wall 8 includes a top portion 8a at a top side and a bottom portion 8b at a bottom side in a height direction (indicated by an arrow H) substantially orthogonal to the flow direction and the width direction. The top portion 8a and the bottom portion 8b of the microflow passage wall 8 are held at a distance from each other in the height direction. The distance between the top portion 8a and the bottom portion 8b in the height direction, is determined to generate the interfacial tension of the liquid for preventing leakage of the liquid flowing in the microflow passage 1 to the sideways ventilation passages 6. The microflow passage 1 opens to the two sideways ventilation passages 6 at both sides in the width direction.

The assay device includes a separating space wall 9 that defines the separating space 3 in cooperation with the first absorbing porous medium 2. The separating space may be defined by further components in addition to the first absorbing porous medium and the separating space wall. The separating space wall 9 includes a top portion 9a and a bottom portion 9b which are positioned at the top side and the bottom side in the height direction, respectively.

The assay device includes a guide wall 10 protruding toward the one side in the flow direction in the housing space 4 from the bottom portion 9b of the separating space wall 9. The guide wall 10 abuts the first absorbing porous medium 2 in the height direction. The bottom portion 9b of the separating space wall 9 and the guide wall 10, and inclines to be apart from the microflow passage 1 in the height direction from the other side to the one side in the flow direction. Note that FIGS. 3 and 11, described later, do not clearly show the inclination of the bottom portion 9b of the separating space wall 9 as it tends to be less than that of the guide wall 10. However, the guide wall may be formed to protrude from the top portion of the separating space wall to the one side in the flow direction in the housing space. In such a case, the top portion of the separating space wall and the guide wall may be separated from the microflow passage in the height direction toward the one side from the other side in the flow direction.

The assay device includes a housing space wall 11 that defines the housing space 4. The assay device includes two sideways ventilation passage walls 12 that define the two sideways ventilation passages 6, respectively. The assay device also includes a connecting ventilation passage wall 13 that defines the connecting ventilation passage 7.

The assay device may be provided with a reaction porous medium 14 to be disposed in the intermediate section 1c of the microflow passage 1. The reaction porous medium 14 is configured to be able to react with the liquid or the substance, such as the specimen and/or the like contained in the liquid. Accordingly, the reaction porous medium 14 may be configured to support the reaction reagent or the like to be used for the assay. In an example, the reaction porous medium 14 may be cellulose which supports the antibody and the antigen. However, it is not limited to the specific type of porous medium. In addition to the reaction porous medium 14, at least one of the top portion and the bottom portion of the microflow passage wall may be configured to be able to react with the liquid or the substance, such as the specimen and/or the like contained in the liquid. The assay device may be configured not to include the reaction porous medium. In such a case, at least one of the top portion and the bottom portion of the microflow passage wall may be configured to be able to react with the liquid or the substance, such as the specimen and/or the like contained in the liquid, as described above.

Detailed Structure of Assay Device

Referring to FIGS. 1 to 5, detailed structures of the assay device according to the Embodiment will be described. Such an assay device may further be configured as follows. The assay device may be configured to have the height direction vertically directed in the usage state. In this case, the top portion and the bottom portion of the assay device are directed upward and downward in the vertical direction, respectively.

The microflow passage 1 is substantially linearly formed. In the present invention, the microflow passage may be formed into a curved or a bent shape. The other end 1b of the microflow passage 1 is defined by the other end 8c of the microflow passage wall 8. The other end 8c of the microflow passage wall 8 is positioned between the microflow passage 1 and the connecting ventilation passage 7.

The height of the microflow passage 1, that is, the distance in the height direction between the top portion 8a and the bottom portion 8b of the microflow passage wall 8 may be in the range from approximately 1 µm to approximately 1000 µm (that is, approximately 1 mm (millimeter)) inclusive. The width d of the microflow passage 1 may be in the range from approximately 100 µm to approximately 10000 µm (that is, approximately 1 cm (centimeter)) inclusive. The length of the microflow passage 1 in the flow direction may be in the range from approximately 10 µm to approximately 10 cm inclusive. The capacity P of the microflow passage 1 may be in the range from approximately 0.1 µl to approximately 1000 µl inclusive. More preferably, it may be in the range from approximately 1 µl or more to less than approximately 500 The respective dimensions and the capacity of the microflow passage are not limited to the abovementioned values.

The first absorbing porous medium 2 has its height greater than that of the microflow passage 1. The first absorbing porous medium 2 protrudes closer to the bottom side than the microflow passage 1 in the height direction. If the guide wall protrudes from the top portion of the separating space wall to the one side in the flow direction in the housing space, the first absorbing porous medium may protrude closer to the top side than the microflow passage in the height direction.

A downstream portion 3a of the separating space 3, which is positioned at the downstream side in the flow direction is closed with the first absorbing porous medium 2. The separating space 3 is communicated with the microflow passage 1 and the two sideways ventilation passages 6 in the flow direction. Specifically, an upstream portion 3b of the separating space 3, which is positioned at the downstream side in the flow direction is communicated with the microflow passage 1 and the two sideways ventilation passages 6 in the flow direction. The top portion 9a of the separating space wall 9 is provided with two ventilation spaces 3c.

The two ventilation spaces 3c are communicated with the two sideways ventilation passages 6, respectively at the upstream side in the flow direction. The top portions 8a, 9a of the microflow passage wall 8 and the separating space wall 9 may linearly extend continuously along the flow direction. The ventilation space 3c allows air ventilation between the separating space 3 and the sideways ventilation passages 6. The two ventilation spaces 3c are positioned outside the microflow passage 1 in the width direction. The distance between the two ventilation spaces 3c in the width direction may be substantially equivalent to the width of the microflow passage 1. The two ventilation spaces 3c may be disposed corresponding to the two sideways ventilation passages 6 in the width direction, respectively. The two ventilation spaces 3c may be communicated with the housing space 4. In particular, the two ventilation spaces 3c may extend to be communicated with the top portion of the housing space 4 in the height direction at the downstream side in the flow direction.

The capacity Q of the separating space 3 may be in a range from approximately 0.001 µl to approximately 10000 µl, inclusive. The ratio of the capacity Q of the separating space 3 to the capacity P of the microflow passage 1, that is, Q/P may be approximately 0.01 or more. The capacity of the separating space, and the ratio of the capacity of the separating space to that of the microflow passage are not limited to the abovementioned values. The capacity Q of the separating space 3 may be more than the capacity P of the microflow passage 1. However, it is possible to set the capacity of the separating space to be equal to or less than the capacity of the microflow passage.

Hydrophilization treatments may be applied to the respective surfaces of the microflow passage wall 8 and the separating space wall 9, which come in contact with the liquid. The hydrophilization treatment may be the optical treatment using plasma, or the treatment using the blocking agent capable of preventing the non-specific conjugate contained in the liquid, if any, from being adsorbed by those surfaces, or may include at least one of the abovementioned treatments. It is possible to use commercial blocking agents, such as Block Ace, bovine serum albumin, casein, skimmed milk, gelatin, surfactants, polyvinyl alcohol, globulin, serum (for example, fetal bovine serum or normal rabbit serum), ethanol, MPC polymer and/or the like as the blocking agent. It is possible to use a single kind of blocking agent, or a mixture of two or more kinds of blocking agents.

The inlet 5 is formed to penetrate through the top portion 8a of the microflow passage wall 8 in the height direction. Each of the sideways ventilation passages 6 is formed to be recessed to the top side and the bottom side of the microflow passage 1 in the height direction. The connecting ventilation passage 7 is formed to be recessed to the bottom side of the microflow passage 1 in the height direction. A top portion 13a of a connecting ventilation passage wall 13 positioned on the top side in the height direction is disposed substantially corresponding to the top portion 8a of the microflow passage wall 8 in the height direction. The two sideways ventilation passages 6 and the connecting ventilation passage 7 may extend continuously to form a substantially U-like shape.

The guide wall 10 is disposed between the first absorbing porous medium 2 and a second absorbing porous medium 15, described later, in the height direction. The guide wall 10 may be disposed to form a tapered shape at the downstream side in the flow direction. The guide wall may be formed into any other shape in a non-restrictive manner.

The reaction porous medium 14 may be formed into a laterally extending narrow shape. The reaction porous medium 14 may be disposed to occupy the region across the entire width of the microflow passage 1. The reaction porous medium 14 may be formed into any other shape, and be freely disposed in a non-restrictive manner.

The assay device includes the second absorbing porous medium 15 in addition to the first absorbing porous medium 2. The second absorbing porous medium 15 is positioned closer to the bottom side than the first absorbing porous medium 2 in the height direction. If the guide wall protrudes toward the one side in the flow direction from the top portion of the separating space wall in the housing space, the second absorbing porous medium 15 may be positioned closer to the top side than the first absorbing porous medium in the height direction. The first and the second absorbing porous media 2, 15 come in contact with each other in the height direction while having the guide wall 10 intervening therebetween. The liquid is fed to the second absorbing porous medium 15 via the first absorbing porous medium 2. The housing space 4 is configured to house the second absorbing porous medium 15 in addition to the first absorbing porous medium 2.

The assay device includes a ventilation passage vent hole 16 which communicates one of the two sideways ventilation passages 6 with the outside of the assay device. The ventilation passage vent hole 16 is formed to allow air circulation from the outside of the assay device to the sideways ventilation passage 6 defined by one of the two sideways ventilation passage walls 12. In particular, the ventilation passage vent hole 16 may be formed to penetrate through a top portion 12a of one of the two sideways ventilation passage walls 12 positioned at the top side in the height direction. The ventilation passage vent hole, however, is not limited to the above-mentioned one. The ventilation passage vent holes may be formed in both of the two sideways ventilation passage walls.

The assay device includes a housing space vent hole 17 which communicates the housing space 4 with the outside of the assay device. The housing space vent hole 17 is formed to penetrate through the housing space wall 11. The housing space vent hole 17 may be positioned at one side in the flow direction in the housing space 4.

A flow passage top-side cavity 18 is formed at the top side of the top portion 8a of the microflow passage wall 8 in the height direction. A flow passage bottom-side cavity 19 is formed at the bottom side of the bottom portion 8b of the microflow passage wall 8 in the height direction. A separating space top-side cavity 20 is formed at the top side of the top portion 9a of the separating space wall 9 in the height direction. A housing space top-side cavity 21 is formed at the top side of a top portion 11a of the housing space wall 11 in the height direction.

One end of the flow passage top-side cavity 18 positioned at the one side in the flow direction is communicated with the separating space top-side cavity 20. The other end of the flow passage top-side cavity 18 positioned at the other side in the flow direction is at a distance from the inlet 5. The flow passage top-side cavity 18 is communicated with the two sideways ventilation passages 6 in the width direction. The flow passage bottom-side cavity 19 is formed corresponding to the microflow passage 1 when viewed in the height direction. The flow passage bottom-side cavity 19 is communicated with the two sideways ventilation passages 6 in the width direction. The flow passage bottom-side cavity 19 is also communicated with the connecting ventilation passage 7 in the flow direction. The separating space top-side cavity 20 is formed corresponding to the top portion 9a of the separating space wall 9 when seen from the height direction. The housing space top-side cavity 21 is disposed at a distance from the separating space top-side cavity 20 in the flow direction. The separating space top-side cavity 20 is communicated with the two ventilation spaces 3c in the width direction. The housing space top-side cavity 21 is communicated with the two ventilation spaces 3c in the height direction.

The assay device includes a window portion 22 configured to allow the reaction porous medium 14 in the microflow passage 1 to be visually observed from the outside of the assay device. The window portion 22 is transparent. The window portion 22 is positioned at the top side of the flow passage top-side cavity 18 in the height direction. The window portion 22 may be positioned corresponding to the intermediate section 1c of the microflow passage 1, in particular, the reaction porous medium 14.

Layered Structure of Assay Device

Figure 1:
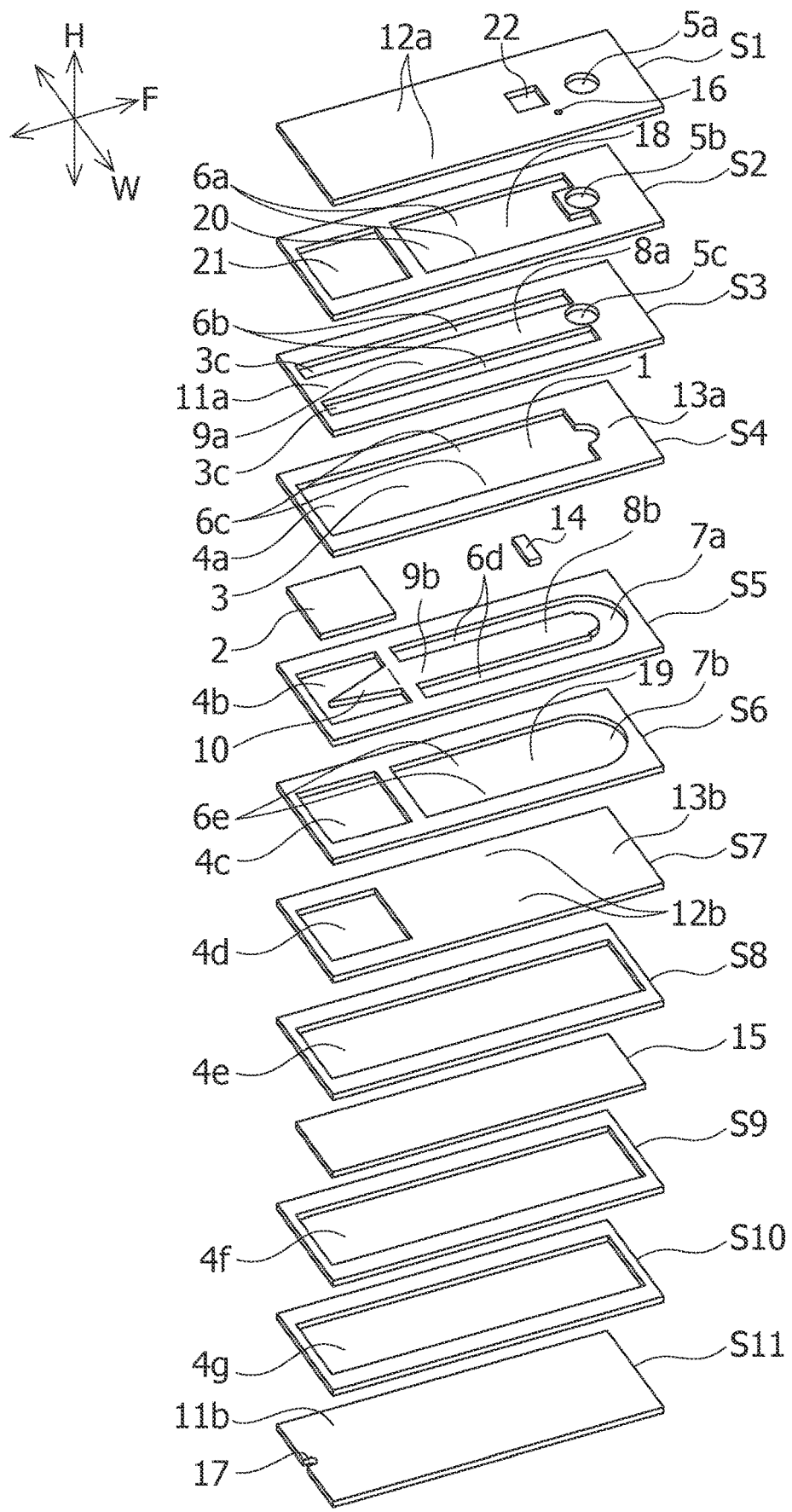
FIG. 1 is a schematic exploded perspective view showing an assay device according to a First Embodiment.

A layered structure of the assay device will be described referring to FIG. 1. In an example, the assay device according to the Embodiment may be formed using a layered structure as described below. Obviously, the assay device may be produced using a structure other than the layered structure.

The assay device includes a top-side casing layer S1, a top-side cavity layer S2, a top-side core layer S3, an intermediate core layer S4, a bottom-side core layer S5, a bottom-side cavity layer S6, an intermediate spacer layer S7, an intermediate adhesion layer S8, a bottom-side spacer layer S9, a bottom-side adhesion layer S10, and a bottom-side casing layer S11, which are sequentially arranged from the top to bottom of the assay device. Each of the top-side casing layer S1, the top-side core layer S3, the bottom-side core layer S5, the intermediate spacer layer S7, the bottom-side spacer layer S9, and the bottom-side casing layer S11 is produced using the material which prevents permeation of the liquid. A contact angle between the top-side core layer S3 and the bottom-side core layer S5 may be less than 90°. The top-side core layer S3 and the bottom-side core layer S5 may be transparent. It is possible to make at least one of the top-side core layer and the bottom-side core layer translucent or opaque. At least one of the top-side core layer S3 and the bottom-side core layer S5 is elastically deformable under the liquid pressure upon passage of the liquid through the assay device.

The top-side casing layer S1, the top-side core layer S3, the bottom-side core layer S5, the intermediate spacer layer S7, the bottom-side spacer layer S9, and the bottom-side casing layer S11 may be produced using plastics. Materials for forming the top-side casing layer S1, the top-side core layer S3, the bottom-side core layer S5, the intermediate spacer layer S7, the bottom-side spacer layer S9, and the bottom-side casing layer S11 may be plastic sheets or plastic films. The plastic material includes polyolefins (PO) such as polyethylene (PE), high density polyethylene (HDPE), and polypropylene (PP), ABS resins (ABS), AS resins (SAN), polyvinylidene chloride (PVDC), polystyrene (PS), polyethylene terephthalate (PET), polyvinyl chloride (PVC), nylon, polymethyl methacrylate (PMMA), cycloolefin copolymer (COC), cycloolefin polymer (COP), polycarbonate (PC), polydimethylsiloxane (PDMS), polyacrylonitrile (PAN), biodegradable plastics such as polylactic acid (PLA), other polymers, or combinations of them. If at least one of the top-side casing layer, the top-side core layer, the bottom-side core layer, the spacer layer, and the bottom-side casing layer is made of the material which does not allow fluid infiltration, it is possible to produce the layer using material other than plastics. The material other than plastics may be resin, glass, metal, and/or the like. It is possible to use either the same or different materials/ingredients for producing the top-side casing layer S1, the top-side core layer S3, the bottom-side core layer S5, the intermediate spacer layer S7, the bottom-side spacer layer S9, and the bottom-side casing layer S11.

Each of the top-side cavity layer S2, the intermediate core layer S4, the bottom-side cavity layer S6, the intermediate adhesion layer S8, and the bottom-side adhesion layer S10 is in the form of a double-sided tape or the layer including the double-sided tape. The respective top and bottom surfaces of these layers S2, S4, S6, S8, S10 exhibit adhesive properties. The top and bottom surfaces of the top-side cavity layer S2 are bonded to the bottom surface of the top-side casing layer S1, and the top surface of the top-side core layer S3, respectively. The top and bottom surfaces of the intermediate core layer S4 are bonded to the bottom surface of the top-side core layer S3 and the top surface of the bottom-side core layer S5, respectively. The top and bottom surfaces of the bottom-side cavity layer S6 are bonded to the bottom surface of the bottom-side core layer S5 and the top surface of the intermediate spacer layer S7, respectively. The top and bottom surfaces of the intermediate adhesion layer S8 are bonded to the bottom surface of the intermediate spacer layer S7 and the top surface of the bottom-side spacer layer S9, respectively. The top and bottom surfaces of the bottom-side adhesion layer S10 are bonded to the bottom surface of the bottom-side spacer layer S9 and the top surface of the bottom-side casing layer S11, respectively.

At least one of the top-side cavity layer, the intermediate core layer, the bottom-side cavity layer, the intermediate adhesion layer, and the bottom-side adhesion layer may be produced using the materials or ingredients which may be used for producing the top-side casing layer, the top-side core layer, the bottom-side core layer, the spacer layer, the bottom-side spacer layer, and the bottom-side casing layer, as described above. In such a case, the adjacent layers may be bonded using bonding means such as the adhesive, the welding, and/or the like. The materials or ingredients to be used for producing at least one of the top-side cavity layer, the intermediate core layer, the bottom-side cavity layer, the intermediate adhesion layer, and the bottom-side adhesion layer may be the same as or different from those used for producing the adjacent layer.

Relationship between Components and Layered Structure of Assay Device

Referring to FIGS. 1, and 3 to 5, an explanation will be made with respect to the relationship between components and the layered structure of the assay device according to the Embodiment, which is produced using the abovementioned layered structure. The microflow passage 1 is formed to penetrate through the intermediate core layer S4 in the height direction. The top-side core layer S3 and the bottom side core layer S5 include the top portion 8a and the bottom portion 8b of the microflow passage wall 8, respectively.

The separating space 3 is formed to penetrate through the intermediate core layer S4 in the height direction. The ventilation space 3c is formed to penetrate through the top-side core layer S3 in the height direction. The top-side core layer S3 includes the top portion 9a of the separating space wall 9. The bottom-side core layer S5 includes the bottom portion 9b of the separating space wall 9. The housing space 4 includes seven through sections 4a, 4b, 4c, 4d, 4e, 4f, 4g, which penetrate through the intermediate core layer S4, the bottom-side core layer S5, the bottom-side cavity layer S6, the intermediate spacer layer S7, the intermediate adhesion layer S8, the bottom-side spacer layer S9, and the bottom-side adhesion layer S10 in the height direction, respectively. The top-side core layer S3 and the bottom-side casing layer S1l include the top portion 11a and the bottom portion 11b of the housing space wall 11, respectively.

The four top-side through sections 4a to 4d of seven through sections 4a to 4g constituting the housing space 4, are formed to ensure housing of the first absorbing porous medium 2. The three bottom-side through sections 4e to 4g are formed to ensure housing of the second absorbing porous medium 15. The second absorbing porous medium 15 may be greater than the first absorbing porous medium 2. In particular, the length of the second absorbing porous medium 15 in the flow direction may be longer than that of the first absorbing porous medium 2.

The inlet 5 is formed to include three through sections 5a, 5b, 5c, which penetrate through the top-side casing layer S1, the top-side cavity layer S2, and the top-side core layer S3 in the height direction, respectively. The bottom-side core layer S5 includes the guide wall 10. The sideways ventilation passage 6 is formed to include five through sections 6a, 6b, 6c, 6d, 6e, which penetrate through the top-side cavity layer S2, the top-side core layer S3, the intermediate core layer S4, the bottom-side core layer S5, and the bottom-side cavity layer S6 in the height direction, respectively. The top-side casing layer S1 and the intermediate spacer layer S7 include the top portion 12a and the bottom portion 12b of the sideways ventilation passage wall 12, respectively. The connecting ventilation passage 7 is formed to include two through sections 7a, 7b, which penetrate through the bottom-side core layer S5 and the bottom-side cavity layer S6 in the height direction, respectively. The intermediate core layer S4 and the intermediate spacer layer S7 include the top portion 13a and the bottom portion 13b of the connecting ventilation passage wall 13, respectively.

The ventilation passage vent hole 16 is formed to penetrate through the top-side casing layer S1 in the height direction, and to communicate one of the two sideways ventilation passage walls 12 with the outside of the assay device. The housing space vent hole 17 is formed to penetrate through the bottom-side casing layer S11 in the height direction, and to communicate the housing space 4 with the outside of the assay device.

The flow passage top-side cavity 18, the separating space top-side cavity 20, and the housing space top-side cavity 21 are formed to penetrate through the top-side cavity layer S2 in the height direction. The flow passage top-side cavity 18, the separating space top-side cavity 20, and the housing space top-side cavity 21 are positioned between the top-side casing layer S1 and the top-side core layer S3 in the height direction. The flow passage bottom-side cavity 19 is formed to penetrate through the bottom-side cavity layer S6 in the height direction. The flow passage bottom-side cavity 19 is positioned between the bottom-side core layer S5 and the intermediate spacer layer S7 in the height direction. The top-side casing layer S1 includes the window portion 22.

Fluid Control in Assay Device

Referring to FIGS. 6(*a*) to 6(*d*), and 7(*a*) to 7(*c*), an explanation will be made with respect to fluid control executed in the assay device according to the Embodiment. Here, liquids applied to the assay device are referred to as first and second liquids L1, L2. In the explanation, the first and second liquids L1, L2 will be supplied to the assay device in this order. The first liquid L1 and the second liquid L2 are different from each other. However, the first liquid and the second liquid may be the same. In FIGS. 6(*a*) to 6(*d*), and 7(*a*) to 7(*d*), solid lines are used, for the purpose of explanation, for indicating the microflow passage 1, the absorbing porous medium 2, the separating space 3, the housing space 4, the inlet 5, the sideways ventilation passages 6, the connecting ventilation passage 7, and the reaction porous medium 14 as well as the first and the second liquids L1, L2.

Typically, each quantity of the liquids (each quantity of the first and the second liquids L1, L2) supplied to the assay device may be equal to or greater than approximately 1 μl, and less than approximately 1 ml. Preferably, each quantity of the liquids is equal to or greater than approximately 1.5 μl, and more preferably, approximately 3.0 μl or more. The upper limit of each quantity of the liquids may be in the range from several μl to several hundreds of ill. Determination of each quantity of the liquids may stabilize detection sensitivity of the specimen and facilitate detection of the specimen and/or the like. In this case, each quantity of the liquids may be obtained by a drop of the liquid. Each quantity of the liquids may be greater than the capacity of the microflow passage 1. In such a case, the liquid may be divided adequately by the separating space 3 into a part absorbed by the absorbing porous medium 2 and another part detained in the microflow passage 1. Each quantity of the liquids may be made less than the capacity of the microflow passage, or substantially equivalent to that of the microflow passage.

First, the first liquid L1 is supplied to the inlet 5 as shown in FIG. 6(*a*). The first liquid L1 then flows into the microflow passage 1. The first liquid L1 further flows in the microflow passage 1 from the upstream side to the downstream side in the flow direction. While the first liquid L1 is flowing in the microflow passage 1, an assay is performed by the reaction porous medium 14. The two sideways ventilation passages 6 are disposed at both sides of the reaction porous medium 14 in the width direction. Air circulation in the two sideways ventilation passages 6 allows the first liquid L1 to flow from the upstream side to the downstream side in the flow direction after passing through the reaction porous medium 14 in the microflow passage 1.

In a case in which supply of the first liquid L1 is continued, in particular, supply of the first liquid L1 by a quantity in excess of the capacity of the microflow passage 1, the first liquid L1 flowing in the microflow passage 1 reaches the separating space 3 as shown in FIG. 6(*b*). The first liquid L1 comes in contact with the absorbing porous medium 2 after passing through the separating space 3. Thereafter, the flow of the first liquid L1 extends from the one end 1*a* of the microflow passage 1 to the absorbing porous medium 2 in the separating space 3 along inner side edges of the two ventilation spaces 3*c* by interfacial tension of the first liquid L1 and the air circulation in the two ventilation spaces 3*c*. The first liquid L1 is absorbed by the absorbing porous medium 2 in the abovementioned state until the supply of the liquid L1 is stopped. When flowing into the separating space 3 from the one end 1*a* of the microflow passage 1, the first liquid L1 moves under the force toward the flow direction based on the lateral flow. The interfacial tension of the first liquid L1 in the abovementioned state at the inner edges of the two ventilation spaces 3*c* becomes significantly greater than the force that directs the first liquid L1 toward the two ventilation spaces 3*c* based on at least one of the lateral flow and the capillary force of the absorbing porous medium 2. Consequently, the first liquid L1 in the abovementioned state ensures prevention of leakage of the first liquid L1 from the ventilation space 3*c*.

After stopping supply of the first liquid L1, the flow of the first liquid L1 is narrowed in the separating space 3 to be away from the inner edges of the two ventilation spaces 3*c* as being directed from the one end 1*a* of the microflow passage 1 and the absorbing porous medium 2 toward the center therebetween in the flow direction, as shown in FIG. 6(*c*). The first liquid L1 is then divided by the separating space 3 into a part absorbed through the capillary force of the absorbing porous medium 2, and another part held in the microflow passage 1 as shown in FIG. 6(*d*).

After stopping supply of the first liquid L1, the second liquid L2 is further supplied to the inlet 5 as shown in FIG. 7(*a*). Similar to the first liquid L1, the supplied second liquid L2 flows in the microflow passage 1. The second liquid L2 extrudes the first liquid L1 which has been preliminarily filled in the microflow passage 1 toward the separating space 3. As a result, solution exchange occurs in the microflow passage 1 by replacing the first liquid L1 with the second liquid L2. The assay is performed by the reaction porous medium 14 in the foregoing while the second liquid L2 is flowing in the microflow passage 1.

In a case in which supply of the second liquid L2 is continued, in particular, supply of the second liquid L2 by a quantity in excess of that of the first liquid L1 which has been preliminarily filled in the microflow passage 1, the first liquid L1 extruded by the second liquid L2 comes in contact with the absorbing porous medium 2 via the separating space 3 as shown in FIG. 7(*b*). The flow of the first liquid L1 extends to reach a convex portion 5 of the absorbing porous medium 2 from the one end 1*a* of the microflow passage 1 in the separating space 3 again. Thereafter, subsequent to the first liquid L1, the second liquid L2 comes in contact with the absorbing porous medium 2 via the separating space 3. Similar to the first liquid L1, the second liquid L2 then flows as shown in FIG. 7(*c*), and is divided by the separating space 3 into the part absorbed through the capillary force of the absorbing porous medium 2 and another part detained in the microflow passage 1 as shown in FIG. 7(*d*).

The solution exchange allows the ELISA process or the like to easily generate multistage antigen-antibody reaction. The solution exchange may be securely executed, in particular, when making quantity of the second liquid L2 supplied to the assay device substantially equal to or greater than that of the first liquid L1 which has been filled in the microflow passage 1.

In other words, in the assay device according to the Embodiment, when supplying multiple kinds of liquid to the inlet 5 sequentially, the microflow passage 1 is preliminarily filled with the preceding one of the multiple kinds of liquid, and supply of the preceding liquid is stopped. Subsequently, another one of the multiple kinds of liquid, which is subsequent to the preceding liquid, is supplied to the inlet 5 so that the preceding liquid can be replaced with the subsequent liquid in the microflow passage 1. The solution exchange for replacing the preceding liquid with the subsequent liquid may be executed repeatedly. In such a case, typically, the preceding liquid is different from the subsequent liquid. The preceding liquid may be the same as the subsequent liquid.

The assay device according to the Embodiment includes the microflow passage 1 configured to allow liquid to flow, the absorbing porous medium 2 disposed at a distance from the one end 1a of the microflow passage 1, and the separating space 3 disposed between the one end 1a of the microflow passage 1 and the absorbing porous medium 2. It is further provided with the two sideways ventilation passages 6 which are adjacent to both sides of the microflow passage 1, respectively in the width direction, and communicated with the microflow passage 1 to allow air circulation.

The liquid in the microflow passage 1 comes in contact with air in the sideways ventilation passage 6 in the width direction. This makes it possible to avoid the contact of the liquid with the wall that defines the microflow passage 1 in the width direction. This may reduce the probability of non-specific adsorption of samples, reagents, impurities and/or the like which adhere on the wall that defines the microflow passage 1, and further reduces the risk of mixture of impurities from adhering to the wall that defines the microflow passage 1 with the liquid. This may avoid the influence of viscosity and friction between the liquid in the microflow passage 1 and the wall that defines the microflow passage 1 in the width direction. As the wall that defines the microflow passage 1 does not exist, it is possible to avoid the influence of intensity or non-uniformity of the force generated when packaging the microflow passage 1 on the flowability of the liquid flowing in the microflow passage 1. It is possible to release an air gap generated in the liquid in the microflow passage 1 into the sideways ventilation passages 6. It is also possible to efficiently supply such gas as nitrogen and oxygen in the sideways ventilation passages 6 to the liquid in the microflow passage 1. As a result, the flowability of the liquid may be improved, resulting in enhanced liquid control performance.

The assay device according to the Embodiment further includes the inlet 5 disposed in the other end 1b of the microflow passage 1 to allow the liquid to be supplied to the microflow passage 1, and the connecting ventilation passage 7 for connecting the two sideways ventilation passages 6 and extending around the inlet 5 to allow air circulation.

The two sideways ventilation passages 6 are connected with the connecting ventilation passage 7 so as to allow efficient air circulation to the two sideways ventilation passages 6 and the connecting ventilation passage 7. Around the inlet 5, it is also possible to reduce the probability of non-specific adsorption of samples, reagents, impurities and/or the like which adhere on the microflow passage wall 8 that defines the microflow passage 1, and further avoid the influence of viscosity and friction between the liquid in the microflow passage 1 and the microflow passage wall 8. This makes it possible to improve flowability of the liquid, resulting in enhanced liquid control performance.

In the assay device according to the Embodiment, the microflow passage wall 8 includes the top portion 8a and the bottom portion 8b for defining the microflow passage 1 in the height direction, and the top portion 8a and the bottom portion 8b of the microflow passage wall 8 are held at a distance from each other in the height direction.

The liquid supplied from the inlet 5 may be securely guided into the microflow passage 1 so as to allow the liquid to flow toward the downstream side from the upstream side in the flow direction in the microflow passage 1. This makes it possible to improve flowability of the liquid, resulting in enhanced liquid control performance.

The assay device according to the Embodiment further includes the reaction porous medium 14 disposed in the microflow passage 1 to react with the liquid or the substance contained in the liquid.

Even if the reaction porous medium 14 is disposed in the microflow passage 1 for confirming the assay reaction, the air circulation in the sideways ventilation passages 6 ensures the liquid flow in the microflow passage 1 while allowing passage of the liquid through the reaction porous medium 14, to makes it possible to enhance the liquid control performance. In addition to or instead of the reaction porous medium, at least one of the top portion and the bottom portion of the microflow passage wall is made able to react with the liquid or the substance, such as the specimen and/or the like contained in the liquid to provide similar functions and effects to those derived from the above-mentioned structure.

The assay device according to the Embodiment includes the housing space 4 for housing the absorbing porous medium 2, the separating space wall 9 for defining the separating space 3 in cooperation with the absorbing porous medium 2, which is provided with the top portion 9a and the bottom portion 9b for defining the separating space 3 at both sides in the height direction, and the guide wall 10 which protrudes to the one side in the flow direction from the bottom portion 9b of the separating space wall 9 in the housing space 4. The guide wall 10 abuts on the absorbing porous medium 2 in the height direction. One of the top portion 9a and the bottom portion 9b of the separating space wall 9, and the guide wall 10 are formed to separate from the microflow passage 1 in the height direction toward the one side from the other side in the flow direction.

As the height of the separating space 3 increases toward the downstream from the upstream of the liquid flow, the liquid may be securely divided by the separating space 3 into the part absorbed by the absorbing porous medium 2 and another part detained in the microflow passage 1. This makes it possible to enhance the liquid control performance.

Second Embodiment

An explanation will be made with respect to an assay device according to a Second Embodiment. The assay device of the Embodiment is similar to that of the First Embodiment except the point to be described below. Explanations of structures of the assay device similar to those of the First Embodiment will be omitted. In this Embodiment, similar components to those of the First Embodiment will be designated with the same reference numerals.

Structure of Assay Device

Referring to FIGS. 8 to 11, an explanation will be made with respect to the structure of the assay device according to the Embodiment. The assay device according to the Embodiment includes a microflow passage 31 and a microflow passage wall 32 that defines the microflow passage 31. The microflow passage 31 and the microflow passage wall 32 according to the Embodiment are similar to the microflow passage 1 and the microflow passage wall 8 according to the First Embodiment, respectively except the point to be described below. The microflow passage wall 32 includes a top portion 32a and a bottom portion 32b for defining the microflow passage 31 in the height direction. As the liquid is supplied from the inlet 5 to the microflow passage 31, in the other end 31b of the microflow passage 31, an abutment state of the top portion 32a and the bottom portion 32b of the microflow passage wall 32 in the height direction is made changeable into a state in which those portions are separated in the height direction. The two sideways ventilation passages 6 may extend along respective side edges 31d of the microflow passage 31 in the width direction.

A connecting ventilation passage 33 according to the Embodiment is similar to the connecting ventilation passage 7 according to the First Embodiment except the point to be described below. The connecting ventilation passage 33 communicates with the other end 31b of the microflow passage 31. The connecting ventilation passage 33 is formed to be recessed to the top-side of the microflow passage 31 in the height direction.

A flow passage top-side cavity 35 according to the Embodiment is similar to the flow passage top-side cavity 18 of the First Embodiment except the point to be described below. The flow passage top-side cavity 35 communicates with the inlet 5. The other end of the flow passage top-side cavity 35 communicates with the connecting ventilation passage 33.

Relationship between Components and Layered Structure of Assay Device

Figure 8:
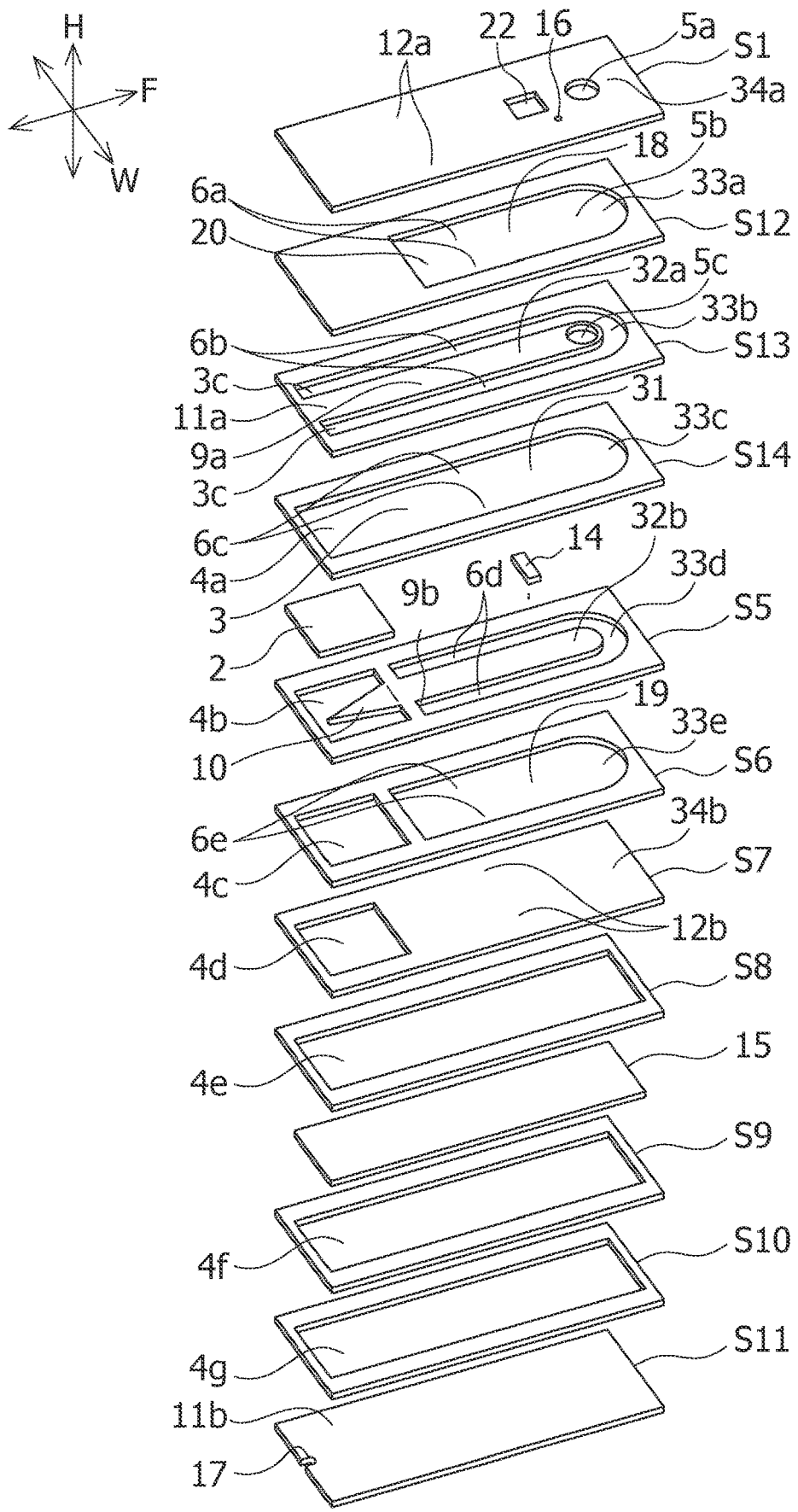
FIG. 8 is a schematic exploded perspective view showing an assay device according to a Second Embodiment.
Figure 9:
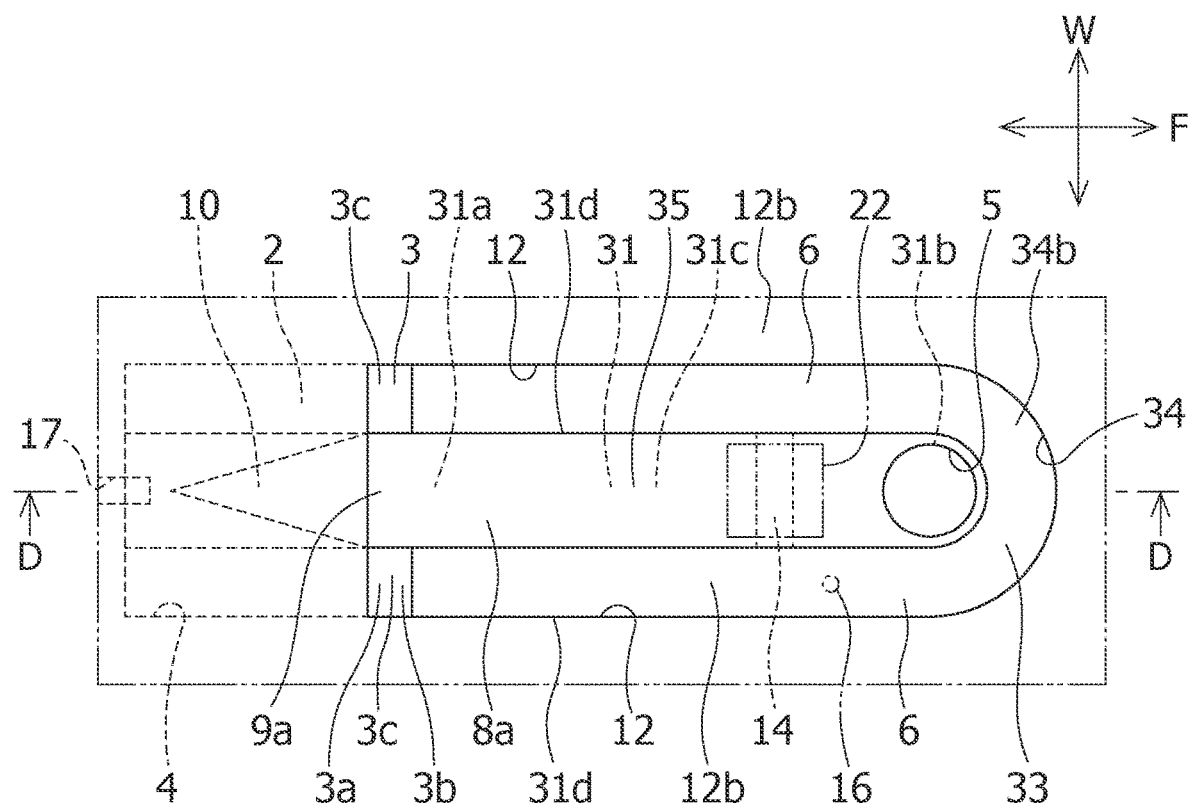
FIG. 9 is a schematic plan view showing the assay device according to the Second Embodiment.
Figure 10:
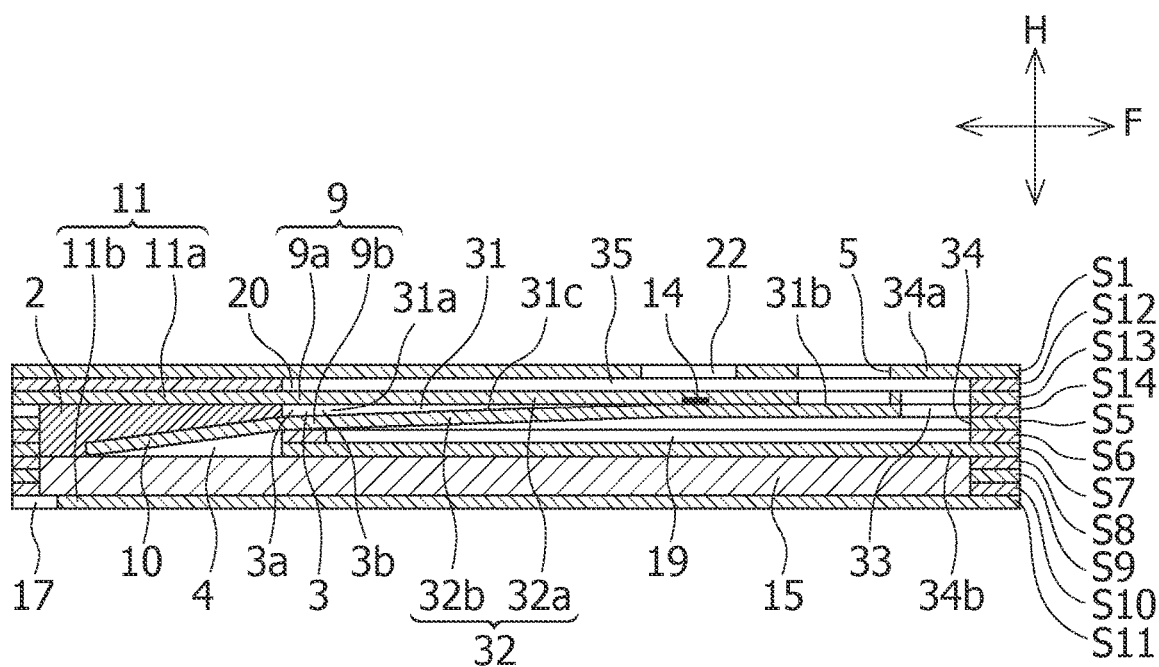
FIG. 10 is a sectional view taken along line D-D of FIG. 9 in the state before supplying the liquid to an inlet of the assay device.
Figure 11:
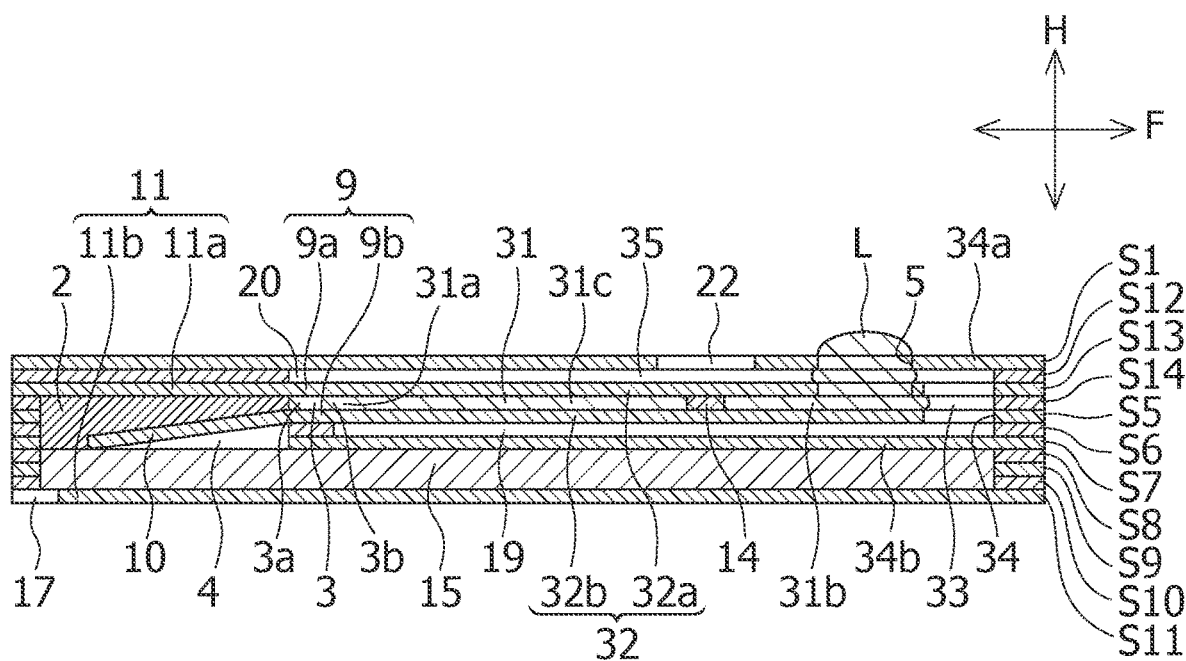
FIG. 11 is a sectional view taken along line D-D of FIG. 9 in the state after supplying the liquid to the inlet of the assay device.

Referring to FIGS. 8, 10 and 11, an explanation will be made with respect to a relationship between components and a layered structure of the assay device according to the Embodiment. The assay device according to the Embodiment includes a top-side cavity layer S12, a top-side core layer S13, and an intermediate core layer S14. The top-side cavity layer S12, the top-side core layer S13, and the intermediate core layer S14 according to the Embodiment are similar to the top-side cavity layer S2, the top-side core layer S3, and the intermediate core layer S4 according to the First Embodiment, respectively, except the point to be described below.

The connecting ventilation passage 33 is formed to include five through sections 33a, 33b, 33c, 33d, 33e, which penetrate through the top-side cavity layer S12, the top-side core layer S13, the intermediate core layer S14, the bottom-side core layer S5, and the bottom-side cavity layer S6, respectively, in the height direction. In the connecting ventilation passage 33 according to the Embodiment, the sections 33d, 33e penetrating through the bottom-side core layer S5 and the bottom-side cavity layer S6 are similar to the sections 7a, 7b penetrating through the bottom-side core layer S5 and the bottom-side cavity layer S6 in the connecting ventilation passage 7 according to the First Embodiment. The top-side casing layer S1 and the intermediate spacer layer S7 include a top portion 34a and a bottom portion 34b of a connecting ventilation passage wall 34, respectively. The top-side cavity layer S12 does not include the housing space top-side cavity 21 according to the First Embodiment.

Fluid Control in Assay Device

Referring to FIGS. 10 and 11, an explanation will be made with respect to the fluid control in the assay device according to the Embodiment. The fluid control in the assay device according to the Embodiment is similar to the fluid control in the assay device according to the First Embodiment, except for the point described below.

The principle of flow of the liquid L in the microflow passage 31 of the assay device according to the Embodiment may have a theoretical basis as described below. The liquid L described herein may be replaced with the first liquid L1 or the second liquid L2 as abovementioned in the First Embodiment. Referring to FIG. 10, before supplying the liquid L, the top portion 32a and the bottom portion 32b of the microflow passage wall 32 are in a partial abutment state in the microflow passage 31. In FIG. 10, as the reaction porous medium 14 is squeezed by the top portion 32a and the bottom portion 32b of the microflow passage wall 32 in an intermediate section 31c of the microflow passage 31, it is expressed as an approximately linear part.

As FIG. 11 shows, upon supply of the liquid L to the inlet 5 of the assay device in the abovementioned state, the top portion 32a and the bottom portion 32b of the microflow passage wall 32 are peeled from each other by the liquid L which flows based on the lateral flow. In the microflow passage 31, peeling charge is generated in the top portions 32a and the bottom portion 32b of the microflow passage wall 32 to attract water molecules, resulting in the surface tension in the liquid L. This allows the liquid L to flow in the microflow passage 31 without reducing the flow rate. The foregoing principle of flow of the liquid L may be a theoretical basis as a possible conceivable example, which is not limited so long as the liquid L is allowed to flow in the microflow passage without reducing its flow rate.

The assay device according to the Embodiment provides similar effects to those derived from the assay device according to the First Embodiment except the effect obtained by maintaining the top portion 32a and the bottom portion 32b of the microflow passage wall 32 separated in the height direction. In the assay device according to the Embodiment, the liquid supplied from the inlet 5 to the microflow passage 31 makes the abutment state of the top portion 32a and the bottom portion 32b of the microflow passage wall 32 in the height direction at the other end 31b of the microflow passage 31 changeable into a state in which these portions are in a separated state in the height direction. This makes it possible to execute the fluid control in the assay device as mentioned above. The flowability of the liquid may be improved, resulting in enhanced liquid control performance.

Third Embodiment

An explanation will be made with respect to an assay device according to a Third Embodiment. The assay device according to this Embodiment is similar to the assay device according to the First Embodiment, except for the point described below. Explanations of similar structures to those of the assay device according to the First Embodiment will be omitted in the Embodiment.

Outline of Structure of Assay Device

Figure 12:
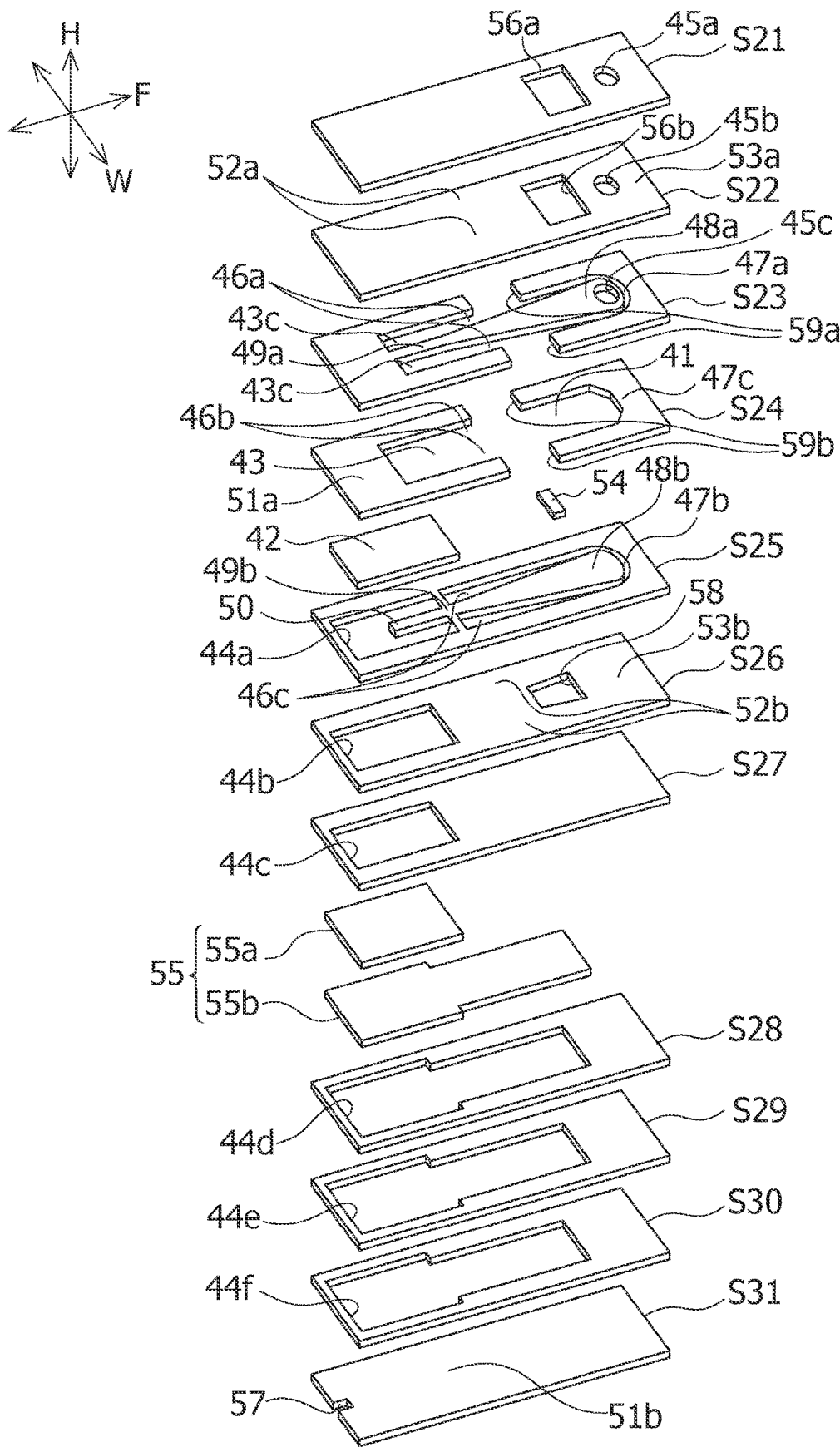
FIG. 12 is a schematic exploded perspective view showing an assay device according to a Third Embodiment.
Figure 13:
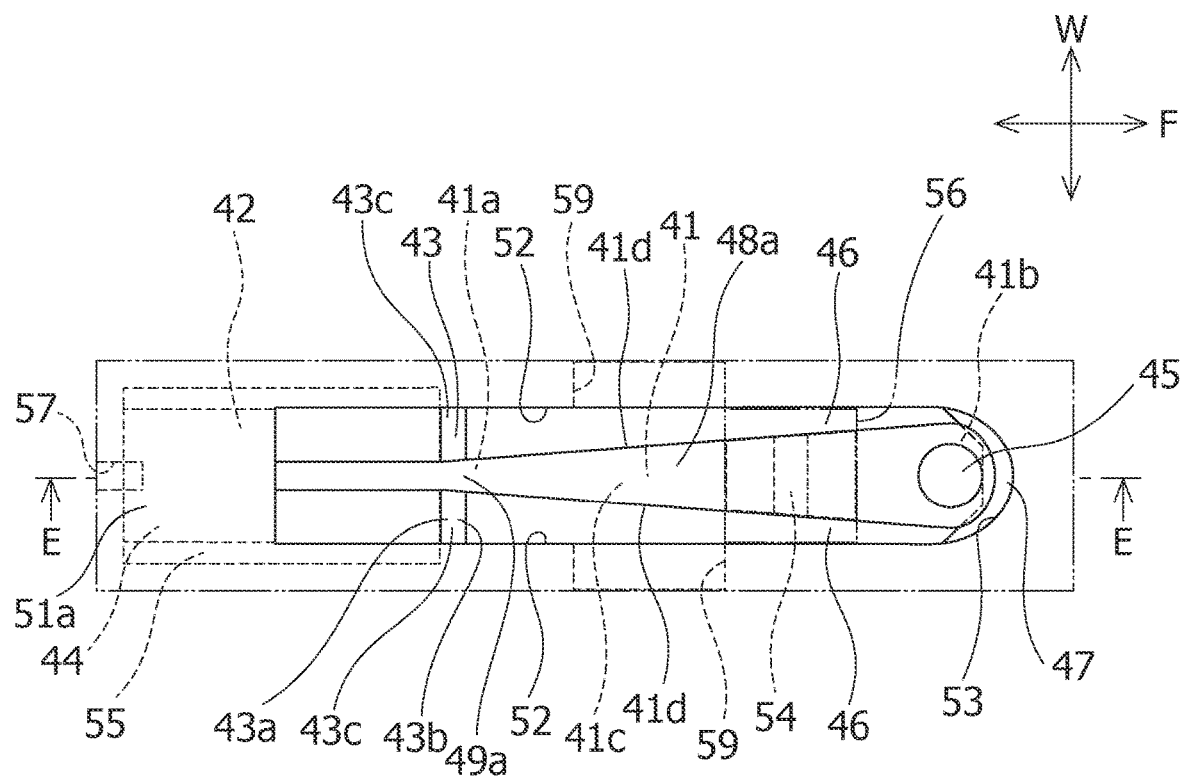
FIG. 13 is a schematic plan view showing the assay device according to the Third Embodiment.
Figure 14:
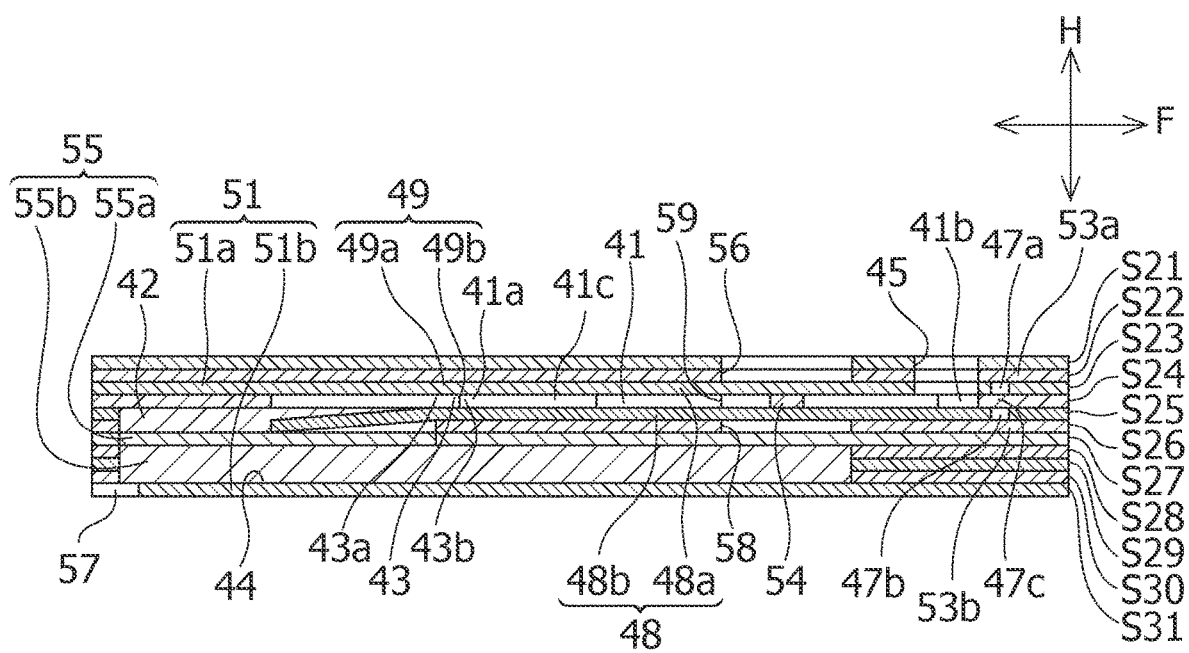
FIG. 14 is a sectional view taken along line E-E of FIG. 13.

Referring to FIGS. 12 to 14, an explanation will be made with respect to an outline of the structure of the assay device according to the Embodiment. The outline of the structure of the assay device according to the Embodiment may be defined similarly to the outline of the structure of the assay device according to the First Embodiment.

In the outline of the structure, a microflow passage 41 of the Embodiment may be defined similarly to the microflow passage 1 of the First Embodiment. One end 41a, the other end 41b, an intermediate section 41c, and side edges 41d of the microflow passage 41 of the Embodiment may be defined similarly to the one end 1a, the other end 1b, the intermediate section 1c, and the side edges 41d of the microflow passage 1 of the First Embodiment.

A first absorbing porous medium 42, a separating space 43, a housing space 44, an inlet 45, two sideways ventilation passages 46, and a connecting ventilation passage 47 may be defined similarly to the first absorbing porous medium 2, the separating space 3, the housing space 4, the inlet 5, the two sideways ventilation passages 6, and the connecting ventilation passage 47 of the First Embodiment, respectively. A microflow passage wall 48 of the Embodiment may be defined similarly to the microflow passage wall 8 of the First Embodiment. A top portion 48a and a bottom portion 48b of the microflow passage wall 48 of the Embodiment may be defined similarly to the top portion 8a and the bottom portion 8b of the microflow passage wall 8 of the First Embodiment, respectively.

A separating space wall 49 of the Embodiment may be defined similarly to the separating space wall 9 of the First Embodiment. A top portion 49a and a bottom portion 49b of the separating space wall 49 of the Embodiment may be defined similarly to the top portion 9a and the bottom portion 9b of the separating space wall 9 of the First Embodiment. A guide wall 50, a housing space wall 51, two sideways ventilation passage walls 52, and a connecting ventilation passage wall 53 according to the Embodiment may be defined similarly to the guide wall 10, the housing space wall 11, the two sideways ventilation passage walls 12, and the connecting ventilation passage wall 13 according to the First Embodiment.

Detailed Structure of Assay Device

Referring to FIGS. 12 to 14, an explanation will be made with respect to detailed structures of the assay device according to the Embodiment. The detailed structures of the assay device according to the Embodiment may be similar to those of the assay device according to the First Embodiment, except for the point described below. The microflow passage 41 is formed to have its width decreased toward one side from the other side in the flow direction. Each of the top portion 48a and the bottom portion 48b of the microflow passage wall 48 is also formed to have its width decreased toward the one side from the other side in the flow direction. The microflow passage 41 and the microflow passage wall 48 allow the liquid to be efficiently divided by the separating space 43 into the part absorbed through the capillary force of the absorbing porous medium 42, and the other part detained in the microflow passage 41.

A downstream portion 43a, an upstream portion 43b, and two ventilation spaces 43c of the separating space 43 of the Embodiment may be defined similarly to the downstream portion 3a, the upstream portion 3b, and the two ventilation spaces 3c of the separating space 3 of the First Embodiment, respectively. The connecting ventilation passage 47 includes a top portion 47a and a bottom portion 47b positioned at the top side and the bottom side of the microflow passage 41 in the height direction, respectively. The connecting ventilation passage 47 is positioned corresponding to the microflow passage 41 in the height direction, and includes a partition portion 47c as a partition between the top portion 47a and the bottom portion 47b in the height direction. The two sideways ventilation passages 46, and the top portion 47a and the bottom portion 47b of the connecting ventilation passage 47 may extend continuously to form a substantially U-like shape. The assay device includes a reaction porous medium 54 defined similarly to the reaction porous medium 14 of the First Embodiment. Similar to the First Embodiment, in addition to the reaction porous medium 54, at least one of the top portion and the bottom portion of the microflow passage wall may be made able to react with the liquid or the substance, such as the specimen and/or the like contained in the liquid. Similar to the First Embodiment, the assay device may be configured to have no reaction porous medium. In such a case, at least one of the top portion and the bottom portion of the microflow passage wall may be made able to react with the liquid or the substance, such as the specimen and/or the like contained in the liquid as in the First Embodiment.

The assay device includes a second absorbing porous medium 55 in addition to the first absorbing porous medium 42. The second absorbing porous medium 55 is positioned closer to the bottom side than the first absorbing porous medium 42 in the height direction. The second absorbing porous medium 55 includes an upstream portion 55a and a downstream portion 55b, which are layered in the height direction. The upstream portion 55a of the second absorbing porous medium 55 is positioned closer to the first absorbing porous medium 42 than the downstream portion 55b in the height direction. If the guide wall protrudes toward one side in the flow direction from the top portion of the separating space wall in the housing space, the second absorbing porous medium may be positioned closer to the top side than the first absorbing porous medium in the height direction. The first and the second absorbing porous media 42, 55 come in contact with each other in the height direction while having the guide wall 50 intervened therebetween. The liquid is designed to be fed to the second absorbing porous medium 55 via the first absorbing porous medium 42. The housing space 44 is configured to house the second absorbing porous medium 55 in addition to the first absorbing porous medium 42.

The assay device includes the reaction porous medium 54 and the second absorbing porous medium 55, which are defined similarly to the reaction porous medium 14 and the second absorbing porous medium 15 according to the First Embodiment, respectively. The assay device also includes a vent hole/window portion 56 which allows the reaction porous medium 54 in the microflow passage 41 to be visually observed from the outside of the assay device. The vent hole/window portion 56 may be positioned corresponding to the intermediate section 41c of the microflow passage 41, in particular, the reaction porous medium 54. The vent hole/window portion 56 is formed to allow air circulation to the two sideways ventilation passages 46 from the outside of the assay device. In particular, the vent hole/window portion 56 may be formed to penetrate through top portions 52a of the two sideways ventilation passage walls 52 positioned at the top side in the height direction. The vent hole/window portion 56 is formed to bypass the top portion 48a of the microflow passage wall 48 which is deformed by the reaction porous medium 54 to protrude toward the top side in the height direction. The vent hole/window portion, however, is not limited to the abovementioned one. The vent hole/window portion may be formed to allow air circulation only to one of the two sideways ventilation passages from the outside of the assay device.

The assay device includes a housing space vent hole 57 which may be defined similarly to the housing space vent hole 17 according to the First Embodiment. The assay device includes a relief cavity 58 adjacent to the bottom side of the bottom portion 48b of the microflow passage wall 48 in the height direction. The relief cavity 58 is positioned corresponding to the vent hole/window portion 56. The relief cavity 58 is formed to bypass the bottom portion 48b of the microflow passage wall 48 which is deformed by the reaction porous medium 54 to protrude toward the bottom side in the height direction.

The assay device includes two side holes 59 which communicate the two sideways ventilation passages 46 with the outside of the assay device, respectively. The two side holes 59 are formed to penetrate the two sideways ventilation passage walls 52 in the width direction, respectively. The respective side holes 59 are positioned corresponding to the microflow passage 41 in the height direction. The respective side holes 59 are configured to allow a shielding member (not shown) for shielding the liquid flow in the microflow passage 41 to be detachably inserted into the microflow passage 41 from the outside of the assay device. The two side holes 59 are positioned corresponding to each other in the flow direction. The respective side holes 59 are positioned in one side relative to the reaction porous medium 54 in the flow direction. The respective side holes 59 may be adjacent to the vent hole/window portion 56 in one side in the flow direction. However, the assay device may be configured to have one side hole which communicates only one of the two sideways ventilation passages with the outside of the assay device.

The assay device according to the Embodiment does not include cavities respectively corresponding to the flow passage top-side cavity 18, the flow passage bottom-side cavity 19, the separating space top-side cavity 20, and the housing space top-side cavity 21 of the assay device according to the First Embodiment. However, the assay device according to the Embodiment may be configured to form a cavity corresponding to at least one of those cavities.

Layered Structure of Assay Device

Referring to FIG. 12, an explanation will be made with respect to the layered structure of the assay device. The assay device according to the Embodiment may be produced using the layered structure as an example to be described below. It is to be understood that the assay device may be produced using the structure other than the layered structure.

The assay device according to the Embodiment includes a top-side casing layer S21, a top-side cavity layer S22, a top-side core layer S23, an intermediate core layer S24, a bottom-side core layer S25, a bottom-side cavity layer S26, an intermediate spacer layer S27, an intermediate adhesion layer S28, a bottom-side spacer layer S29, a bottom-side adhesion layer S30, and a bottom-side casing layer S31, which are defined similarly to the top-side casing layer S1, the top-side cavity layer S2, the top-side core layer S3, the intermediate core layer S4, the bottom-side core layer S5, the bottom-side cavity layer S6, the intermediate spacer layer S7, the intermediate adhesion layer S8, the bottom-side spacer layer S9, the bottom-side adhesion layer S10, and the bottom-side casing layer S1*l* of the assay device according to the First Embodiment, respectively.

Relationship Between Components and Layered Structure of Assay Device

Referring to FIGS. 12 and 14, an explanation will be made with respect to a relationship between components and the layered structure of the assay device according to the Embodiment in the case in which the assay device is produced using the layered structure as described above. The relationship between the components and the layered structure of the assay device according to the Embodiment is similar to the relationship between the components and the layered structure of the assay device according to the First Embodiment, except for the point described below.

The housing space 44 is formed to have six through sections 44a, 44b, 44c, 44d, 44e, 44f, which penetrate the bottom-side core layer S25, the bottom-side cavity layer S26, the intermediate spacer layer S27, the intermediate adhesion layer S28, the bottom-side spacer layer S29, and the bottom-side adhesion layer S30 in the height direction, respectively. The intermediate core layer S24 and the bottom-side casing layer S31 include a top portion 51a and a bottom portion 51b of the housing space wall 51, respectively.

The two top-side through sections 44a, 44b of the six through sections 44a to 44f constituting the housing space 44 are formed to ensure housing of the first absorbing porous medium 42. The four bottom-side through sections 44c to 44f are formed to ensure housing of the second absorbing porous medium 55. The top-side through section 44c of those four through sections 44c to 44f is formed to ensure housing of the upstream portion 55a of the second absorbing porous medium 55. The three bottom-side through sections 44d to 44f of those four through sections 44c to 44f are formed to ensure housing of the downstream portion 55b of the second absorbing porous medium 55.

The second absorbing porous medium 55 may be greater than the first absorbing porous medium 42. In particular, the length of the second absorbing porous medium 55 in the flow direction may be longer than that of the first absorbing porous medium 42. The upstream portion 55a of the second absorbing porous medium 55 may have the length in the flow direction substantially the same as that of the first absorbing porous medium 42 in the flow direction, and the downstream portion 55b of the second absorbing porous medium 55 may have the length in the flow direction longer than that of the first absorbing porous medium 42 in the flow direction.

The inlet 45 is formed to include three through sections 45a, 45b, 45c, which penetrate through the top-side casing layer S21, the top-side cavity layer S22, and the top-side core layer S23 in the height direction, respectively. Each of the sideways ventilation passages 46 is formed to include three through sections 46a, 46b, 46c, which penetrate through the top-side core layer S23, the intermediate core layer S24, and the bottom-side core layer S25 in the height direction, respectively.

The top-side cavity layer S22 and the bottom-side cavity layer S26 include the top portions 52a and the bottom portions 52b of the sideways ventilation passage wall 52, respectively. The top portion 47a and the bottom portion 47b of the connecting ventilation passage 47 penetrate through the top-side core layer S23 and the bottom-side core layer S25 in the height direction, respectively. The intermediate core layer S24 includes the partition portion 47c of the connecting ventilation passage 47. The top-side cavity layer S22 and the bottom-side cavity layer S26 include the top portion 53a and the bottom portion 53b of the connecting ventilation passage wall 53, respectively.

The vent hole/window portion 56 includes two through sections 56a, 56b which penetrate through the top-side casing layer S21 and the top-side cavity layer S22 in the height direction, respectively. The housing space vent hole 57 is formed to penetrate through the bottom-side casing layer S1*l* in the height direction, and communicates the housing space 44 with the outside of the assay device. The relief cavity 58 is formed to penetrate through the bottom-side cavity layer S26 in the height direction. The respective side holes 59 are formed to include two through sections 59a, 59b, which penetrate through the top-side core layer S23 and the intermediate core layer S24 in the height direction. The two side holes 59 communicate the two sideways ventilation passages 46 with the outside of the assay device, respectively.

The fluid may be controlled in the assay device according to the Embodiment similarly to the assay device according to the First Embodiment. The assay device of the Embodiment provides similar effects to those derived from the assay device according to the First Embodiment.

The assay device according to the Embodiment includes the side holes 59 which communicate at least one of the two sideways ventilation passages 46 with the outside of the assay device. The side holes 59 are positioned corresponding to the microflow passage 41 in the height direction. The side holes 59 allow the shielding member (not shown) for shielding the liquid flow in the microflow passage 41 to be detachably inserted into the microflow passage 41 from the outside of the assay device.

As the Embodiments according to the present invention have been described in the nonrestrictive manner, the present invention may be varied and modified based on the technical concept.

EXAMPLES

First Example

In a First Example, the assay device configured according to the First Embodiment as shown in FIGS. 1 to 5 was used to perform solution exchange between blue-colored methylene blue dyeing liquid and transparent phosphate buffer solution. Specifically, operations of supplying the blue-colored methylene blue dyeing liquid, and then the transparent phosphate buffer solution to the inlet 5 of the assay device were performed repeatedly by 10 times. In a series of operations, fluidity of the liquid in the assay device, the liquid absorbing level of the convex portion 5 of the absorbing porous medium 2, and the meniscus in the one end 1a of the microflow passage 1 in the assay device were confirmed.

In the First Example, it was confirmed with respect to secure flows of the methylene blue dyeing liquid and the phosphate buffer solution in the assay device, performance of the absorbing porous medium 2 to securely absorb the methylene blue dyeing liquid and the phosphate buffer solution, and suppression of the meniscus tortuosity in the one end 1a of the microflow passage 1 in the assay device. It was further confirmed with respect to reduction in the residual liquid in the separating space 3. Consequently, it was confirmed that the solution exchange was securely performed between the methylene blue dyeing liquid and the phosphate buffer solution.

Second Example

In a Second Example, the same assay device as the abovementioned one in the First Example was used to perform the solution exchange among transparent phosphate buffer solution, red-colored eosin, and blue-colored methylene blue dyeing liquid. Specifically, first, the transparent phosphate buffer solution was supplied to the inlet 5 of the assay device. Upon passage of approximately 3 minutes after stopping supply of the phosphate buffer solution, the red-colored eosin was supplied to the inlet 5 of the assay device. Upon passage of approximately 3 minutes after stopping supply of the eosin, the transparent phosphate buffer solution was supplied to the inlet 5 of the assay device. Upon passage of approximately 3 minutes after stopping supply of the phosphate buffer solution, the blue-colored methylene blue dyeing liquid was supplied to the inlet 5 of the assay device. In a series of operations, fluidity of the liquid in the assay device, the liquid absorbing level of the absorbing porous medium 2, and the meniscus in the one end 1a of the microflow passage 1 in the assay device were confirmed.

In the Second Example, it was confirmed with respect to secure flows of the phosphate buffer solution, the eosin, and the methylene blue dyeing liquid in the assay device, performance of the absorbing porous medium 2 to securely absorb the phosphate buffer solution, the eosin, and the methylene blue dyeing liquid, and suppression of the meniscus curvature in the one end 1a of the microflow passage 1 in the assay device. It was further confirmed with respect to reduction in the residual liquid in the separating space 3. Consequently, it was confirmed that the solution exchange was securely performed among the phosphate buffer solution, the eosin, and the methylene blue dyeing liquid.

Third Example

In a Third Example, the same assay device as the abovementioned one in the First Example was used to perform the solution exchange among transparent HRP (horseradish peroxidase) labelled antibody solution, transparent phosphate buffer solution, and transparent TMB (3,3',5,5'-tetramethylbenzidine) solution. The TMB solution is a coloring reagent using HRP as enzyme. Specifically, first, the transparent HRP labeled antibody solution was supplied to the inlet 5 of the assay device. Upon passage of approximately 3 minutes after stopping supply of the HRP labeled antibody solution, the transparent phosphate buffer solution was supplied to the inlet 5 of the assay device. Upon passage of approximately 3 minutes after stopping supply of the phosphate buffer solution, the transparent TMB solution was supplied to the inlet 5 of the assay device. In a series of operations, it was confirmed with respect to fluidity of the liquid in the assay device, the liquid absorbing level of the absorbing porous medium 2, and the meniscus in the one end 1a of the microflow passage 1 in the assay device.

In the Third Example, it was confirmed with respect to secure flows of the HRP labeled antibody solution, the phosphate buffer solution, and the TMB solution in the assay device, performance of the absorbing porous medium 2 to securely absorb the HRP labeled antibody solution, the phosphate buffer solution, and the TMB solution, suppression of the meniscus curvature in the one end 1a of the microflow passage 1 in the assay device. It was further confirmed with respect to reduction in the residual liquid in the separating space 3. Consequently, it was confirmed that the solution exchange was securely performed among the HRP labeled antibody solution, the phosphate buffer solution, and the TMB solution.

Fourth Example

Figure 15:
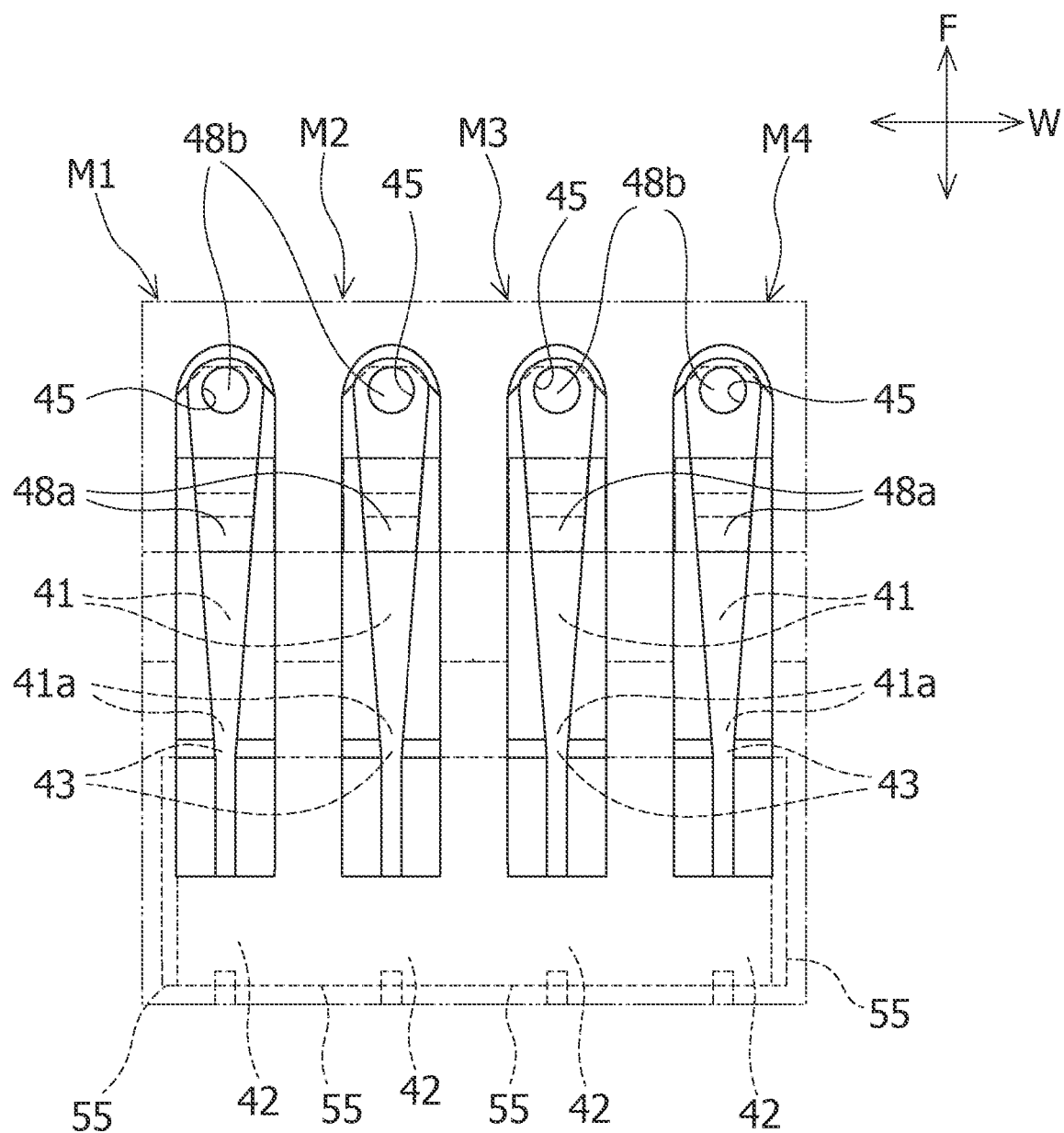
FIG. 15 is a schematic plan view showing an assay system according to a Fourth Example.

In a Fourth Example, the solution exchange was performed in an assay system configured by laterally arranging and combining four assay devices according to the Third Embodiment, including a first assay device M1, a second assay device M2, a third assay device M3, and a fourth assay device M4 as shown in FIG. 15. Referring to FIG. 15, the first to the fourth assay devices M1 to M4 were arranged in the width direction in this order. In the assay system, the first absorbing porous media 42 of the first to the fourth assay devices M1 to M4 were integrally connected in the width direction, and the second absorbing porous media 55 of the first to the fourth assay devices M1 to M4 were integrally connected in the width direction as well.

A pretreatment process was applied to the assay system before performing the solution exchange as described below. In the process of producing the assay system, before laminating the layers S21 to S31 for constituting the four assay devices M1 to M4, approximately 20 μL of the antibody solution was prepared by containing the antiadiponectin antibody (GeneTex, Anti-Adiponectin, Mouse (B863M), No. GTX44473) in the phosphate buffer solution with density of approximately 20 μg/mL. The resultant antibody solution was applied to surfaces of the top portions 48a and the bottom portions 48b of the microflow passage walls 48 for defining the microflow passages 41, and left overnight in a sealed condition. The antiadiponectin antibody was brought into the solid phase on the surfaces of the top portions 48a and the bottom portions 48b of the microflow passage walls 48.

The layers S21 to S31 for constituting the first to the fourth assay devices M1 to M4 were laminated, and two droplet drops of approximately 30 μL of cleaning solution prepared by containing a surfactant (Tween20) in the phosphate buffer solution were supplied to each of the inlets 45 of the respective assay devices M1 to M4. Furthermore, approximately 30 μL of stabilizing solution (Surmodics, StabilCoat) was supplied to each of the inlets 45 of the respective assay devices M1 to M4. The devices were dried in the state in which the supernatant of the stabilizing solution was aspirated, and kept in the environment at the temperature of approximately 4° C. until the start of assay.

The solution exchange to be described below was performed in the pretreated assay system. The solution exchange was performed using adiponectin derived from the adiponectin kit (CircuLex Human Adiponectin ELISA Kit produced by Medical & Biological Laboratories, Co., Ltd.), the HRP labeled antibody solution, and the TMB solution.

First, the two droplet drops of the cleaning solution were supplied to each of the inlets 45 of the respective assay devices M1 to M4. Then the adiponectin was contained in the phosphate buffer solution to prepare approximately 30 μL of the first, the second, the third, and the fourth adiponectin solutions with densities of approximately 0 ng/mL, 40 ng/mL, 80 ng/mL, and 160 ng/mL, respectively. The first to the fourth adiponectin solutions were supplied to the inlets 45 of the first to the fourth assay devices M1 to M4, respectively. Upon passage of approximately 10 minutes after stopping supply of the first to the fourth adiponectin solutions, three droplet drops of the cleaning solution were supplied to each of the inlets 45 of the respective assay devices M1 to M4.

The HRP labeled antibody solution was supplied to each of the inlets 45 of the respective assay devices M1 to M4 by approximately 30 μL. Upon passage of approximately 7.5 minutes after stopping supply of the HRP labeled antibody solution, five droplet drops of the cleaning solution were supplied to each of the inlets 45 of the respective assay devices M1 to M4. The TMB solution was supplied to each of the inlets 45 of the respective assay devices M1 to M4 by approximately 30 μL. Upon passage of approximately 10 minutes after stopping supply of the TMB solution, the state of the assay system was confirmed.

In the Fourth Example, it was confirmed with respect to secure flows of the cleaning solution, the adiponectin solution, the HRP labeled antibody solution, and the TMB solution in the assay system, performance of the first and the second absorbing porous media 42, 55 to securely absorb the cleaning solution, the adiponectin solution, the HRP labeled antibody solution, and the TMB solution, darkening of each color of the first and the second absorbing porous media 42, 55 toward the fourth assay device M4 from the first assay device M1 in the width direction, and suppression of each meniscus curvature in the one ends 41a of the microflow passages 41 in the respective assay devices M1 to M4. It was further confirmed with respect to reduction in the residual liquid in each of the separating spaces 43. Consequently, it was confirmed that the solution exchange was securely performed among the cleaning solution, the adiponectin solution, the HRP labeled antibody solution, and the TMB solution.

REFERENCE SIGNS LIST 1, 31, 41 . . . Microflow passage
1a, 31a, 41a . . . One end
1b, 31b, 41b . . . The other end
2, 42 . . . First absorbing porous medium
3, 43 . . . Separating space
4, 44 . . . Housing space
5, 45 . . . Inlet
6, 46 . . . Sideways ventilation passage
7, 33, 47 . . . Connecting ventilation passage
8, 32, 48 . . . Microflow passage wall
8a, 32a, 48a . . . Top portion
8b, 32b, 48b . . . Bottom portion
9, 49 . . . Separating space wall
9a, 49a . . . Top portion
9b, 49b . . . Bottom portion
10, 50 . . . Guide wall
14, 54 . . . Reaction porous medium
59 . . . Side hole

The invention claimed is:

1. An assay device comprising:
a microflow passage configured to allow liquid to flow;
an absorbing porous medium disposed at a distance from one end of the microflow passage, the one end being positioned on one side in a flow direction of the liquid;
a separating space disposed between the one end of the microflow passage and the absorbing porous medium;
two sideways ventilation passages adjacent to both sides of the microflow passage, respectively in a width direction orthogonal to the flow direction, the two sideways ventilation passages in communication with the microflow passage to allow air circulation;
a housing space housing the absorbing porous medium;
a separating space wall defining the separating space in cooperation with the absorbing porous medium, the separating space wall comprising a top portion and a bottom portion defining the separating space on both sides in a height direction orthogonal to the flow direction and the width direction; and
a guide wall protruding to the one side in the flow direction from the top portion or the bottom portion of the separating space wall in the housing space, wherein
the guide wall abuts the absorbing porous medium in the height direction, and
the top portion or the bottom portion of the separating space wall, and the guide wall are formed to separate from the microflow passage in the height direction toward the one side from the other side in the flow direction.

2. The assay device according to claim 1, further comprising:
an inlet disposed in another end of the microflow passage on another side in the flow direction, the inlet allowing the liquid to be supplied to the microflow passage; and a connecting ventilation passage connecting the two sideways ventilation passages and extending around the inlet to allow air circulation.

3. The assay device according to claim 2, further comprising a microflow passage wall defining the microflow passage, wherein the microflow passage wall comprises a top portion and a bottom portion defining the microflow passage in a height direction orthogonal to the flow direction and the width direction, and the top portion and the bottom portion of the microflow passage wall are held at a distance from each other in the height direction.

4. The assay device according to claim 2, further comprising a microflow passage wall defining the microflow passage, wherein the microflow passage wall comprises a top portion and a bottom portion defining the microflow passage in a height direction orthogonal to the flow direction and the width direction; and the liquid supplied from the inlet to the microflow passage, makes a state in which the top portion and the bottom portion of the microflow passage wall abut each other in the height direction in the another end of the microflow passage, be changed into a state in which the top portion and the bottom portion are held at a distance in the height direction.

5. The assay device according to claim 1, further comprising a reaction porous medium disposed in the microflow passage, the reaction porous medium configured to react with the liquid or a specimen contained in the liquid.

6. The assay device according to claim 1, further comprising a side hole communicating at least one of the two sideways ventilation passages with an exterior of the assay device, wherein the side hole is positioned corresponding to the microflow passage in a height direction.

7. The assay device according to claim 1, wherein the two sideways ventilation passages extend along the flow direction of the microflow passage over an entire length in the flow direction of the microflow passage.

8. The assay device according to claim 1, wherein the two sideways ventilation passages are in communication with the microflow passage without any wall between the sideways ventilation passages and the microflow passage.

9. The assay device according to claim 1, wherein the guide wall has a tapered shape toward the absorbing porous medium.

* * * * *

UNITED STATES PATENT AND TRADEMARK OFFICE
CERTIFICATE OF CORRECTION

| | | |
|---|---|---|
| PATENT NO. | : 12,326,445 B2 | Page 1 of 1 |
| APPLICATION NO. | : 17/269876 | |
| DATED | : June 10, 2025 | |
| INVENTOR(S) | : Yusuke Fuchiwaki | |

It is certified that error appears in the above-identified patent and that said Letters Patent is hereby corrected as shown below:

In the Specification

Column 7, Line 61: Please correct "500 The" to read --500 µl. The--

Column 12, Line 27: Please correct "S1l" to read --S11--

Column 13, Line 38: Please correct "ill" to read --µl--

Column 21, Line 49: Please correct "S1l" to read --S11--

Column 22, Line 56: Please correct "S1l" to read --S11--

Signed and Sealed this
Seventh Day of October, 2025

John A. Squires
*Director of the United States Patent and Trademark Office*